United States Patent
Motterlini et al.

(10) Patent No.: US 9,944,669 B2
(45) Date of Patent: Apr. 17, 2018

(54) FUMARATE-CO-RELEASING MOLECULE HYBRIDS, THEIR USE IN THE TREATMENT OF INFLAMMATORY OR CARDIOVASCULAR DISEASES AND THEIR PROCESS OF PREPARATION

(71) Applicants: UNIVERSITE PARIS EST CRETEIL VAL DE MARNE, Creteil (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR)

(72) Inventors: Roberto Motterlini, Paris (FR); Roberta Foresti, Paris (FR); Thierry Martens, La Quene en Brie (FR); Michael Rivard, Creteil (FR)

(73) Assignees: UNIVERSITE PARIS EST CRETEIL VAL DE MARNE, Creteil (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 15/127,674

(22) PCT Filed: Mar. 20, 2015

(86) PCT No.: PCT/EP2015/056024
§ 371 (c)(1),
(2) Date: Sep. 20, 2016

(87) PCT Pub. No.: WO2015/140337
PCT Pub. Date: Sep. 24, 2015

(65) Prior Publication Data
US 2017/0174716 A1 Jun. 22, 2017

(30) Foreign Application Priority Data
Mar. 21, 2014 (EP) .................................... 14305408

(51) Int. Cl.
*C07F 15/06* (2006.01)
*C07F 15/00* (2006.01)
*C07F 13/00* (2006.01)

(52) U.S. Cl.
CPC ............. *C07F 15/06* (2013.01); *C07F 13/00* (2013.01); *C07F 15/0046* (2013.01)

(58) Field of Classification Search
CPC ....... C07F 15/06; C07F 13/00; C07F 15/0046
See application file for complete search history.

(56) References Cited

U.S. PATENT DOCUMENTS

2010/0105770 A1  4/2010 Motterlini et al.
2013/0203753 A1  8/2013 Cundy et al.

FOREIGN PATENT DOCUMENTS

| WO | WO 02/092075 A2 | 11/2002 |
| WO | WO 2008/003953 A1 | 1/2008 |
| WO | WO 2012/076696 A1 | 6/2012 |
| WO | WO 2013/013179 A1 | 1/2013 |

OTHER PUBLICATIONS

D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
I.V. Turko et al., Pharmacological Reviews, 619-634 (2002).*
F.A. Scappaticci et al., 99 Journal of the National Cancer Institute, 1232-1239 (2007).*
C. Ha et al., 104 The American Journal of Gastroenterology, 1445-1451 (2009).*
C. Yang et al., 1282 Brain Research, 133-141 (2009).*
R. Motterlini et al., 20 Antioxidants & Redox Signaling, 1810-1826 (2014).*
S. Kalinin et al., 263 Journal of Neuroimmunology, 13-19 (2013).*
R. Foresti et al., 76 Pharmacological Research, 132-148 (2013).*
A. Yabluchanskiy et al., 40 Critical Care Medicine, 544-552 (2012).*
J. Wilson et al., 20 Chemistry—A European Journal, 14698-14704 (2014).*
S. Lin et al., 3 ASN Neuro, 75-84 (2011).*
Denmark et al., "Tandem [4+2]/[3+2] Cycloadditions of Nitroalkenes. 9. Synthesis of (−)-Rosmarinecine," J. Am. Chem. Soc., vol. 118, No. 35, 1996, pp. 8266-8277.
Foresti et al., "Small Molecule Activators of the Nrf2-HO-1 Antioxidant Axis Modulate Heme Metabolism and Inflammation in BV2 Microglia Cells," Pharmacological Research, vol. 76, 2013, pp. 132-148.
International Search Report (form PCT/ISA/210), dated Jun. 1, 2015, for International Application No. PCT/EP2015/056024.

(Continued)

*Primary Examiner* — Alexander R Pagano
(74) *Attorney, Agent, or Firm* — Birch, Stewart, Kolasch & Birch, LLP

(57) ABSTRACT

The present invention relates to hybrid fumarate-CO-releasing molecules capable of increasing heme oxygenase-1 (HO-1) activity and HO-1 protein expression and simultaneously releasing CO, their synthesis and their use in therapeutic applications, in particular their use in the treatment of inflammatory or cardiovascular diseases.

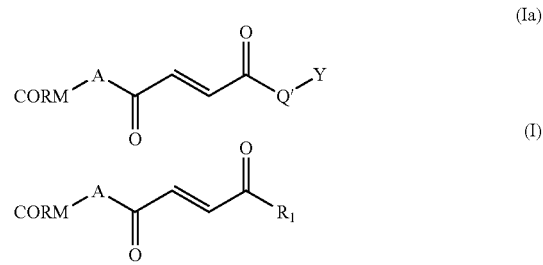

19 Claims, 12 Drawing Sheets

(56) References Cited

OTHER PUBLICATIONS

Shi et al., "Synthesis of Well-Defined Figure-of-Eight-Shaped Polymers by a Combination of ATRP and Click Chemistry," Macromolecular Rapid Communications, vol. 29, 2008, pp. 1672-1678.

Wilson et al., "Design and Synthesis of New Hybrid Molecules that Activate the Transcription Factor Nrf2 and Simultaneously Release Carbon Monoxide," Chem. Eur. J., vol. 20, 2014 (Published online Sep. 15, 2014), pp. 14698-14704.

Wuts et al., "Greene's Protective Groups in Organic Synthesis," Fourth Edition, Table on Contents, John Wiley & Sons, Hoboken, New Jersey, 2007, Total 3 pages.

Zhu et al., "Reactions of Linked Tetrahedron Clusters [Co2(CO)6(μ-HC2CH2O)-]2R with Rh2(C0)4Cl2 to Give Mixed-metal Linked Alkyne-bridged Butterfly Clusters Containing C2Co2Rh2 Unit," Journal of Organometallic Chemistry, vol. 691, No. 3, 2006 (Online Oct. 18, 2005), pp. 485-490, XP028047957.

Alcaraz et al., "Carbon Monoxide-Releasing Molecules: A Pharmacological Expedient to Counteract Inflammation," Current Pharmaceutical Design, vol. 14, No. 5, 2008, pp. 465-472.

Ashrafian et al., "Fumarate is Cardioprotective via Activation of the Nrf2 Antioxidant Pathway," Cell Metabolism, vol. 15, Mar. 7, 2012, pp. 361-371.

Beckman et al., "Inhaled carbon monoxide reduced leukocytosis in a murine model of sickle cell disease," American Journal of Physiology—Heart and Circulatory Physiology, vol. 297, No. 4, Oct. 2009 (Published online Jul. 17, 2009), pp. H1243-H1253 (22 pages).

Christou et al., "Prevention of Hypoxia-Induced Pulmonary Hypertension by Enhancement of Endogenous Heme Oxygenase-1 in the Rat," Circulation Research, vol. 86, 2000, pp. 1224-1229.

De Backer et al., "Water-soluble CO-releasing molecules reduce the development of postoperative ileus via modulation of MAPK/HO-1 signalling and reduction of oxidative stress," Gut, vol. 58, 2009 (Published Online Nov. 20, 2008), pp. 347-356 (11 pages total).

Draheim et al., "Activation of the Astrocytic Nrf2/ARE System Ameliorates the Formation of Demyelinating Lesions in a Multiple Sclerosis Animal Model," GLIA, vol. 64, No. 12, 2016 (Published online Sep. 19, 2016), pp. 2219-2230.

Ferrándiz et al., "Treatment with a CO-releasing molecule (CORM-3) reduces joint inflammation and erosion in murine collagen-induced arthritis," Annals of the Rheumatic Diseases, vol. 67, 2008 (Published online Dec. 6, 2007), pp. 1211-1217 (8 pages total).

Ghoreschi et al., "Fumarates improve psoriasis and multiple sclerosis by inducing type II dendritic cells," The Journal of Experimental Medicine, vol. 208, No. 11, Oct. 10, 2011, pp. 2291-2303 (18 pages total).

Grochot-Przeczek et al., "Heme Oxygenase-1 Accelerates Cutaneous Wound Healing in Mice," PLoS One, vol. 4, Issue 6, e5803, Jun. 4, 2009, pp. 1-16.

Hegazi et al., "Carbon monoxide ameliorates chronic murine colitis through a heme oxygenase 1-dependent pathway," The Journal of Experimental Medicine, vol. 202, No. 12, Dec. 19, 2005, pp. 1703-1713.

Hervera et al., "Carbon Monoxide Reduces Neuropathic Pain and Spinal Microglial Activation by Inhibiting Nitric Oxide Synthesis in Mice," PLoS One, vol. 7, Issue 8, e43693, Aug. 22, 2012, pp. 1-10.

Hinkel et al., "Heme Oxygenase-1 Gene Therapy Provides Cardioprotection Via Control of Post-Ischemic Inflammation," Journal of the American College of Cardiology, vol. 66, No. 2, Jul. 14, 2015, pp. 154-165.

Ishii et al., "Transcription Factor Nrf2 Plays a Pivotal Role in Protection against Elastase-Induced Pulmonary Inflammation and Emphysema," The Journal of Immunology, vol. 175, 2005, pp. 6968-6975 (9 pages total).

Kobayashi et al., "Regulatory Role of Heme Oxygenase 1 in Inflammation of Rheumatoid Arthritis," Arthritis & Rheumatism, vol. 54, No. 4, Apr. 2006, pp. 1132-1142.

Lancel et al., "Carbon Monoxide Improves Cardiac Function and Mitochondrial Population Quality in a Mouse Model of Metabolic Syndrome," PLoS One, vol. 7, Issue 8, e41836, Aug. 1, 2012, pp. 1-11.

Lancel et al., "Carbon Monoxide Rescues Mice from Lethal Sepsis by Supporting Mitochondrial Energetic Metabolism and Activating Mitochondrial Biogenesis," The Journal of Pharmacology and Experimental Therapeutics, vol. 329, No. 2, 2009 (downloaded Apr. 24, 2009), pp. 641-648.

Lastres-Becker et al., "Repurposing the NRF2 Activator Dimethyl Fumarate as Therapy Against Synucleinopathy in Parkinson's Disease," Antioxidants & Redox Signaling, vol. 25, No. 2, 2016, pp. 61-77.

Liu et al., "Heme oxygenase-1 (HO-1) inhibits postmyocardial infarct remodeling and restores ventricular function," The FASEB Journal, vol. 20, Feb. 2006, pp. 207-216.

Long et al., "An Essential Role of NRF2 in Diabetic Wound Healing," Diabetes, vol. 65, Mar. 2016, pp. 780-793.

Motterlini et al., "Heme Oxygenase-1-Derived Carbon Monoxide Contributes to the Suppression of Acute Hypertensive Responses In Vivo," Circ. Res., vol. 83, Sep. 7, 1998, pp. 568-577.

Nakao et al., "Immunomodulatory effects of inhaled carbon monoxide on rat syngeneic small bowel graft motility," Gut, vol. 52, 2003, pp. 1278-1285.

Nakao et al., "Low-dose carbon monoxide inhibits progressive chronic allograft nephropathy and restores renal allograft function," Am. J. Physiol. Renal Physiol., vol. 297, Jul. 2009 (First Published Apr. 15, 2009), pp. F19-F26 (9 pages total).

Ndisang et al., "Upregulation of the heme oxygenase system ameliorates postprandial and fasting hyperglycemia in type 2 diabetes," Am. J. Physiol. Endocrinol. Metab., vol. 296, May 2009 (First published Feb. 10, 2008), pp. E1029-E1041 (14 pages total).

Rojo et al., "NRF2 deficiency replicates transcriptomic changes in Alzheimer's patients and worsens APP and TAU pathology," Redox Biology, vol. 13, 2017 (Available online Jul. 5, 2017), pp. 444-451.

Tamion et al., "Induction of Heme-oxygenase-1 Prevents the Systemic Responses to Hemorrhagic Shock," Am. J. Respir. Crit. Care Med., vol. 164, 2001, pp. 1933-1938.

Tertil et al., "Nrf2-heme oxygenase-1 axis in mucoepidermoid carcinoma of the lung: Antitumoral effects associated with downregulation of matrix metalloproteinases," Free Radical Biology and Medicine, vol. 89, 2015 (Available online Sep. 21, 2015), pp. 147-157.

Uruno et al., "The Keap1-Nrf2 System Prevents Onset of Diabetes Mellitus," Molecular and Cellular Biology, vol. 33, No. 15, Aug. 2013 (Published ahead of print May 28, 2013), pp. 2996-3010.

Vítek et al., "Antiproliferative effects of carbon monoxide on pancreatic cancer," Digestive and Liver Disease, vol. 46, 2014 (Available online Jan. 14, 2014), pp. 369-375.

Wang et al., "Carbon Monoxide-Activated Nrf2 Pathway Leads to Protection Against Permanent Focal Cerebral Ischemia," Stroke, vol. 42, 2011 (Published online Aug. 18, 2011), pp. 2605-2610 (9 pages total).

Wegiel et al., "Carbon Monoxide Expedites Metabolic Exhaustion to Inhibit Tumor Growth," Cancer Research, vol. 73, No. 23, 2013 (Published online Oct. 11, 2013), pp. 7009-7021 (14 pages total).

Yet et al., "Cardiac-Specific Expression of Heme Oxygenase-1 Protects Against Ischemia and Reperfusion Injury in Transgenic Mice," Circulation Research, vol. 89, 2001, pp. 168-173.

Yonchuk et al., "Characterization of the Potent, Selective Nrf2 Activator, PSTC, in Cellular and In Vivo Models of Pulmonary Oxidative Stress," JPET Fast Forward, ASPET Journals, JPET #241794, Aug. 8, 2017, pp. 1-50.

* cited by examiner

FIGURE 2
Fig. 2A
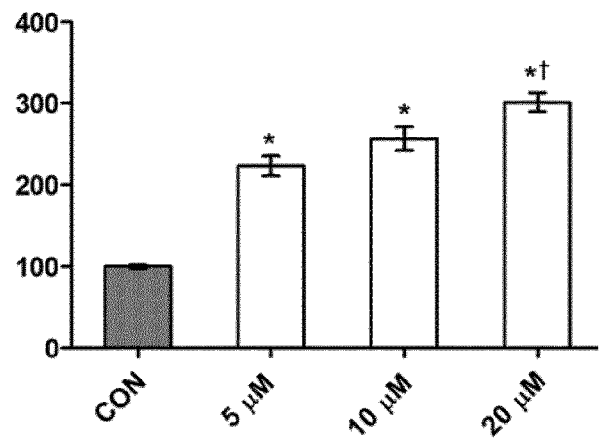
Fig. 2B
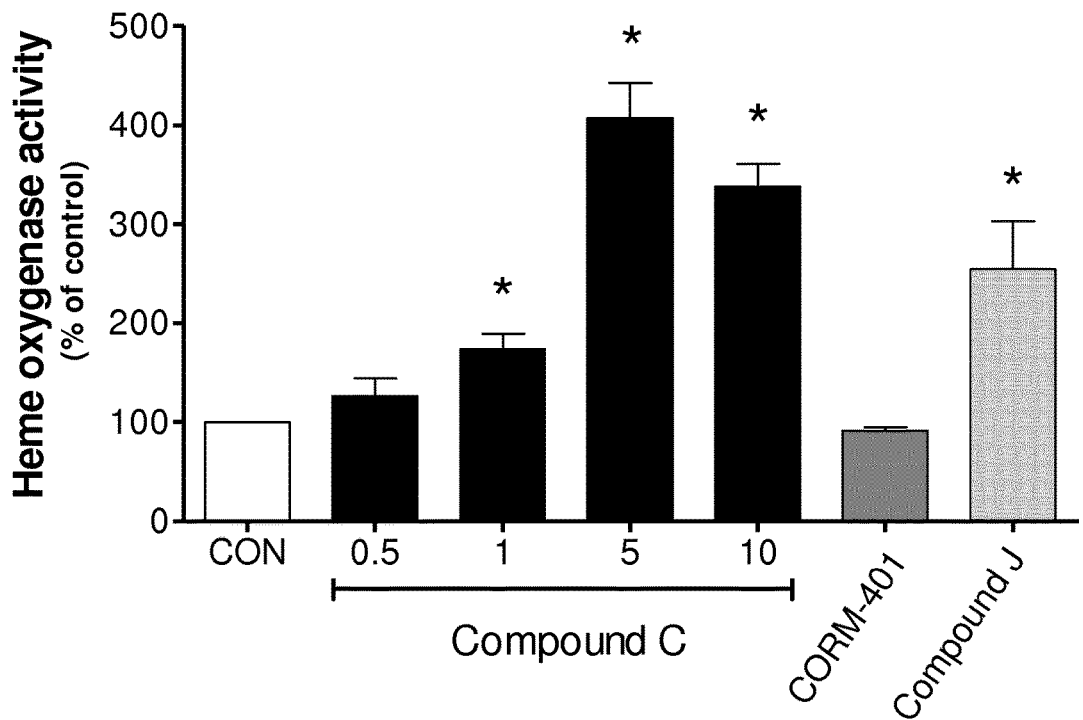

FIGURE 5
Fig. 5A
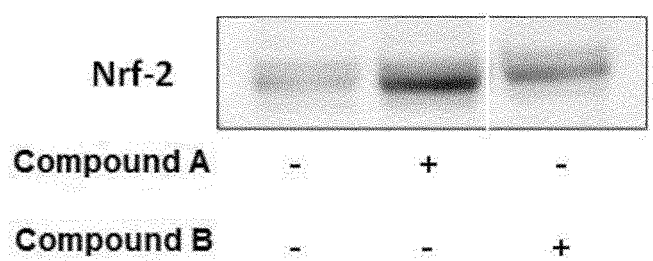
Fig. 5B
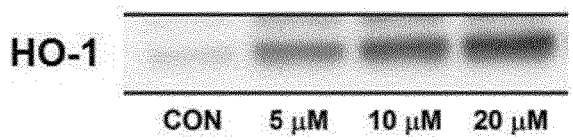
Fig. 5C
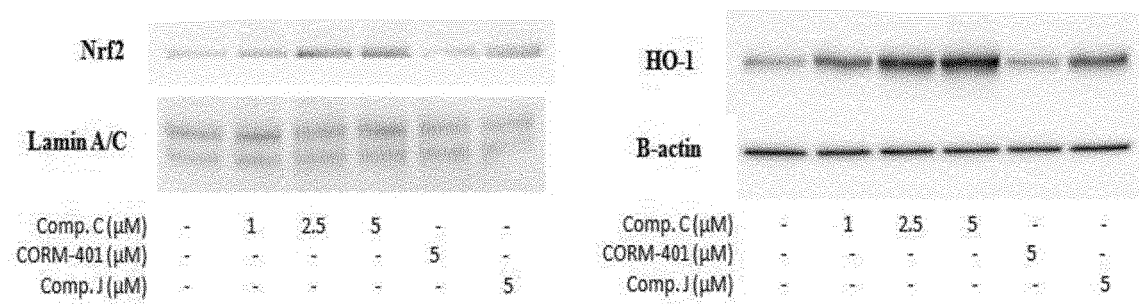

FUMARATE-CO-RELEASING MOLECULE HYBRIDS, THEIR USE IN THE TREATMENT OF INFLAMMATORY OR CARDIOVASCULAR DISEASES AND THEIR PROCESS OF PREPARATION

FIELD OF THE INVENTION

The present invention relates to hybrid fumarate-CO-releasing molecules capable of activating heme oxygenase-1 (HO-1) activity and HO-1 protein expression, their synthesis and their use in therapeutic applications, in particular their use in the treatment of inflammatory and cardiovascular diseases.

BACKGROUND ART

The HO-1/CO system is a significant part of the defense against the damage inflicted by a variety of stress conditions mediated by heavy metals, reactive oxygen species, lipopolysaccharide (LPS) and other inflammatory processes, thereby playing a pivotal role in the regulation of the cytoprotective and anti-inflammatory responses.

CO gas administered at low doses (250 ppm) for restricted period of times has been shown to reproduce (restore) many of the beneficial effects of HO-1 in models of cardiovascular dysfunction, pulmonary hypertension, and inflammatory conditions such as sepsis and inflammatory bowel disease.

Because of the interest in HO-1/CO therapeutic potential, compounds that liberate controlled amounts of CO (CO-releasing molecules, CO-RMs) to biological systems have been developed and demonstrated to exert a wide array of pharmacological effects related to CO release. The vast majority of pharmacologically active CO-RMs described in the literature are metal carbonyls containing either Ru, Fe, Mn, Co and Mo.

The transcription factor Nrf2 is a crucial initiator of the cellular stress response as it co-ordinates the expression of several antioxidant and detoxification genes that repair damage and restore cellular homeostasis. As part of this inducible response, heme oxygenase-1 (HO-1) plays a prominent role by utilizing heme to produce CO, biliverdin/bilirubin and iron, important signaling and protective molecules against oxidative stress and inflammation.

Many chemicals have been identified to act as Nrf2/HO-1 activators and among them several naturally-derived compounds having an α,β-unsaturated carbonyl functionality, including curcumin, the first chemical found to increase HO-1 expression, and chalcones. The list of Nrf2/HO-1 activators has now grown to include several hundred compounds. Because of their mechanism of action, Nrf2/HO-1 activators require time to mount the cellular stress response, resulting in a delayed, albeit essential, beneficial effect.

The synthesis of a molecule possessing both the ability to rapidly release CO and simultaneously stimulate a longer-lasting Nrf2-dependent protective proteome, offers significant therapeutic advantages compared to CO-RMs or Nrf2 activating agents alone in diseases where these pathways are crucial for tissue protection, and there is therefore a need for such molecules.

Zhu et al. (*J. Organomet. Chem.* 2006, 691, 485-490) discloses compound $[Co_2(CO_6)(\mu H_2CCH_2O)-]_2(CO)_2$, however referring only to its use in mixed metal linked alkyne bridged butterfly clusters containing $C_2Co_2R_2$, with applications in the synthesis of polymeric materials.

WO 2012/076696 discloses curcumin derivatives bound to a CO-releasing molecule. The inventors of the present invention have however shown that these molecules do not release carbon monoxide. This lack of CO-release results in molecules that do not exhibit the wide array of beneficial therapeutic effects related to the activation of HO-1 by CO.

WO 2008/003953 also describes CO-releasing molecules of formula (I): $Mn(CO)_4XY$ wherein X and Y are monodentate ligands, or taken together form a bidentate ligand, for the therapeutic delivery of CO to humans and animals. More specifically, WO 2008/003953 discloses CO-releasing compound 364, wherein X represents O(O)CCH2CH2C(O)OH and Y represents Br. However, this molecule demonstrated poor CO-releasing abilities.

Unexpectedly, it has been discovered that hybrid molecules comprising a fumarate moiety and a CO-releasing molecule (CORM) are capable of rapidly liberating CO and activating the Nrf2/HO-1 pathway, resulting in a dual activation of the inflammatory defenses in cells and an improved therapeutic efficacy.

The present invention concerns both compounds with one CORM moiety (mono-CORM compounds) and with two CORM moieties (bi-CORM compounds). The inventors have discovered that both types of molecules have improved therapeutic activities. Moreover, it has been observed that mono-CORM molecules release very quickly high levels of CO, thus exerting a "burst effect". On the other hand, bi-CORM compounds release higher levels of CO (in particular because of the presence of a second CORM moiety), but less rapidly and over a longer period of time. Therefore, mono-CORM compounds of the invention will be used when a "burst effect" is sought for, while bi-CORM compounds of the invention will be used when a sustained release over a long period of time is more appropriate for the patient or with regard to the disease or condition to be treated.

The present invention therefore concerns hybrid fumarate-carbon monoxide releasing molecules (fumarate-CORM), their pharmaceutically acceptable salts, hydrates and solvates, of formula (I):

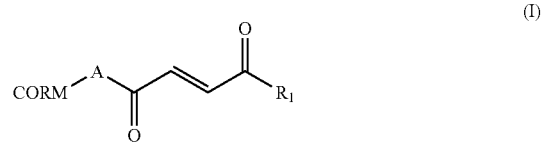

wherein:
A represents:
  a single bond, or
  —Z-Q-, where:
    Q represents O, S or $NR_2$, where $R_2$ represents H, $(C_1\text{-}C_6)$alkyl, aryl, heteroaryl, $(C_1\text{-}C_6)$alkyl-aryl, $(C_1\text{-}C_6)$alkyl-heteroaryl or $(C_1\text{-}C_6)$alkyl-$(C_3\text{-}C_6)$heterocyclyl, —$(C_3\text{-}C_{14})$cycloalkyl, or $R_2$ and Z are connected to form a $(C_3\text{-}C_6)$heterocyclyl,
    Z represents —$(C_1\text{-}C_6)$alkyl-, —$(C_2\text{-}C_6)$alkenyl-, -aryl-, -heteroaryl-, —$(C_2\text{-}C_6)$alkynyl-, —$(C_3\text{-}C_6)$heterocyclyl-, —$(C_3\text{-}C_{14})$cycloalkyl, —$(C_1\text{-}C_6)$alkyl-$R_3$—$(C_1\text{-}C_6)$alkyl-, —$(C_2\text{-}C_6)$alkenyl-$R_3$—$(C_1\text{-}C_6)$alkyl-, —$(C_1\text{-}C_6)$alkyl-$R_3$—$(C_2\text{-}C_6)$alkenyl-, —$(C_2\text{-}C_6)$alkenyl-$R_3$—$(C_2\text{-}C_6)$alkenyl-, —$(C_1\text{-}C_6)$alkyl-$R_3$—$(C_2\text{-}C_6)$alkynyl-, —$(C_2\text{-}C_6)$alkynyl-$R_3$—$(C_2\text{-}C_6)$alkynyl-, —$(C_2\text{-}C_6)$alkynyl-$R_3$—$(C_2\text{-}C_6)$alkynyl-, —$(C_2\text{-}C_6)$alkynyl-$R_3$—$(C_2\text{-}C_6)$alkynyl-$R_3$—$(C_1\text{-}C_6)$alkyl-, —$(C_2\text{-}C_6)$alkynyl-$R_3$—$(C_2\text{-}C_6)$alkenyl-, —$(C_1\text{-}C_6)$alkyl-OCO—, or —$CH_2$—$(CHOR_3)$ CH$_2$O—(C$_1$-C$_6$)alkyl-, where R$_3$ represents aryl, heteroaryl, (C$_3$-C$_6$)heterocyclyl, or (C$_3$-C$_{14}$)cycloalkyl, CORM represents a carbonyl metal complex chosen from among:

Mn(CO)$_5$,

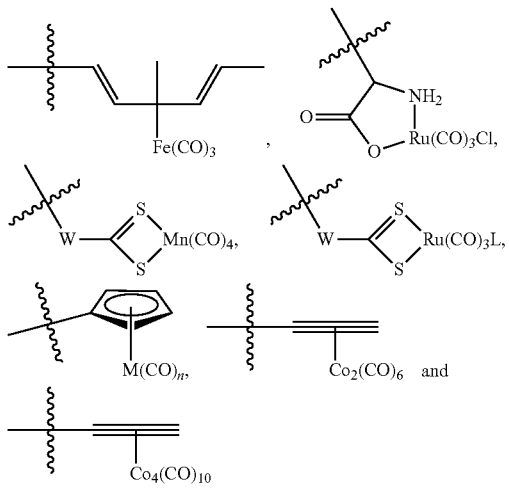

where W represents O or NR$_4$, where R$_4$ represents —(C$_1$-C$_6$)alkyl-,

L represents an ionic ligand such as halogen, or a counter-ion such as BF$_4$ or PF$_6$, M represents Rh, Co, Ru, Mn, Mo, V or Fe, preferably Co, Ru or Mn, and n is an integer chosen so that the metal M has no free valency, preferably, CORM represents a carbonyl metal complex chosen from among:

Mn(CO)$_5$,

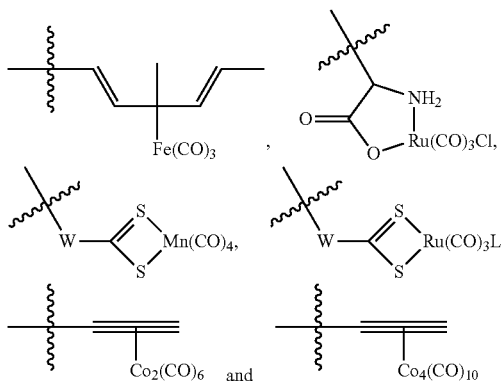

where W represents O or NR$_4$, where R$_4$ represents —(C$_1$-C$_6$)alkyl-,

L represents an ionic ligand such as halogen, or a counter-ion such as BF$_4$ or PF$_6$, and R$_1$ represents:
-Q'-Y, where
Q' represents O, S or NR$_5$, where R$_5$ represents H, (C$_1$-C$_6$)alkyl, aryl, heteroaryl, (C$_1$-C$_6$)alkyl-aryl, (C$_1$-C$_6$)alkyl-heteroaryl or (C$_1$-C$_6$)alkyl-(C$_3$-C$_8$)heterocyclyl, —(C$_3$-C$_{14}$)cycloalkyl, Y represents H, —(C$_1$-C$_6$)alkyl, —(C$_2$-C$_6$)alkenyl, -aryl, -heteroaryl, —(C$_2$-C$_6$)alkynyl, —(C$_3$-C$_8$)heterocyclyl, —(C$_3$-C$_{14}$)cycloalkyl, —(C$_1$-C$_6$)alkyl-R$_6$—(C$_1$-C$_6$)alkyl, —(C$_2$-C$_6$)alkenyl-R$_6$—(C$_1$-C$_6$)alkyl, —(C$_1$-C$_6$)alkyl-R$_6$—(C$_2$-C$_6$)alkenyl, —(C$_2$-C$_6$)alkenyl-R$_6$—(C$_2$-C$_6$)alkenyl, —(C$_1$-C$_6$)alkyl-R$_6$—(C$_2$-C$_6$)alkynyl, —(C$_2$-C$_6$)alkenyl-R$_7$—(C$_2$-C$_6$)alkynyl, —(C$_2$-C$_6$)alkynyl-R$_6$—(C$_2$-C$_6$)alkynyl, —(C$_2$-C$_6$)alkynyl-R$_6$—(C$_1$-C$_6$)alkyl, —(C$_2$-C$_6$)alkynyl-R$_6$—(C$_2$-C$_6$)alkenyl, (C$_1$-C$_6$)alkyl-R$_6$, —(C$_2$-C$_6$)alkenyl-R$_6$, —(C$_2$-C$_6$)alkynyl-R$_6$, where R$_6$ represents aryl, heteroaryl, (C$_3$-C$_8$)heterocyclyl, or (C$_3$-C$_{14}$)cycloalkyl, —CH$_2$(CHOR$_6$)CH$_2$—OR$_7$, where R$_7$ represents H, (C$_1$-C$_6$)alkyl, aryl, heteroaryl, (C$_1$-C$_6$)alkyl-aryl, (C$_1$-C$_6$)alkyl-heteroaryl, (C$_1$-C$_6$)alkyl-(C$_3$-C$_6$)heterocyclyl, (C$_1$-C$_6$)alkyl-(C$_3$-C$_{14}$)cycloalkyl, or, A'-CORM' where A' and CORM' are as defined respectively for A and CORM.

Advantageously, CORM is chosen from among:
Mn(CO)$_5$,

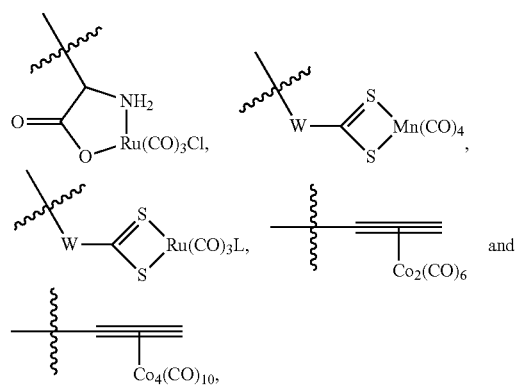

more advantageously from among:

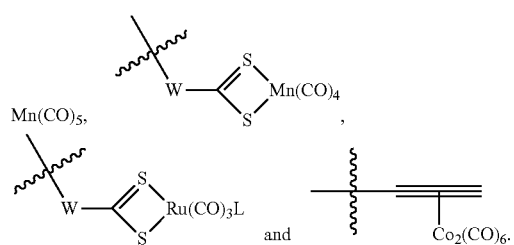

even more advantageously from among

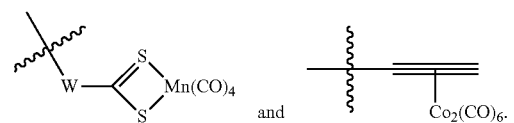

The present invention preferably concerns hybrid fumarate-carbon monoxide releasing molecules (fumarate-CORM), their pharmaceutically acceptable salts, hydrates and solvates, of formula (I) above, wherein:

A represents:
  a single bond, or
  —Z-Q-, where:
    Q represents O, S or $NR_2$, where $R_2$ represents H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, —$(C_3-C_{14})$cycloalkyl, or $R_2$ and Z are connected to form a $(C_3-C_8)$heterocyclyl,
    Z represents —$(C_1-C_6)$alkyl-, —$(C_2-C_6)$alkenyl-, -aryl-, -heteroaryl-, —$(C_2-C_6)$alkynyl-, —$(C_3-C_6)$heterocyclyl-, —$(C_3-C_{14})$cycloalkyl, —$(C_1-C_6)$alkyl-$R_3$—$(C_1-C_6)$alkyl-, —$(C_2-C_6)$alkenyl-$R_3$—$(C_1-C_6)$alkyl-, —$(C_1-C_6)$alkyl-$R_3$—$(C_2-C_6)$alkenyl-, —$(C_2-C_6)$alkenyl-$R_3$—$(C_2-C_6)$alkenyl-, —$(C_1-C_6)$alkyl-$R_3$—$(C_2-C_6)$alkynyl-, —$(C_2-C_6)$alkenyl-$R_3$—$(C_2-C_6)$alkynyl-, —$(C_2-C_6)$alkynyl-$R_3$—$(C_2-C_6)$alkynyl-, —$(C_2-C_6)$alkynyl-$R_3$—$(C_1-C_6)$alkyl-, —$(C_2-C_6)$alkynyl-$R_3$—$(C_2-C_6)$alkenyl-, —$(C_1-C_6)$alkyl-OCO—, or —$CH_2$—$(CHOR_3)$$CH_2O$—$(C_1-C_6)$alkyl-, where $R_3$ represents aryl, heteroaryl, $(C_3-C_8)$heterocyclyl, or $(C_3-C_{14})$cycloalkyl,
$R_1$ represents:
  -Q'-Y, where
    Q' represents O, S or $NR_5$, where $R_5$ represents H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, —$(C_3-C_{14})$cycloalkyl,
    Y represents H, —$(C_1-C_6)$alkyl, —$(C_2-C_6)$alkenyl, -aryl, -heteroaryl, —$(C_2-C_6)$alkynyl, —$(C_3-C_8)$heterocyclyl, —$(C_3-C_{14})$cycloalkyl, —$(C_1-C_6)$alkyl-$R_6$—$(C_1-C_6)$alkyl, —$(C_2-C_6)$alkenyl-$R_6$—$(C_1-C_6)$alkyl, —$(C_1-C_6)$alkyl-$R_6$—$(C_2-C_6)$alkenyl, —$(C_2-C_6)$alkenyl-$R_6$—$(C_2-C_6)$alkenyl, —$(C_1-C_6)$alkyl-$R_6$—$(C_2-C_6)$alkynyl, —$(C_2-C_6)$alkenyl-$R_7$—$(C_2-C_6)$alkynyl, —$(C_2-C_6)$alkynyl-$R_6$—$(C_2-C_6)$alkynyl, —$(C_2-C_6)$alkynyl-$R_6$—$(C_1-C_6)$alkyl, —$(C_2-C_6)$alkynyl-$R_6$—$(C_2-C_6)$alkenyl, $(C_1-C_6)$alkyl-$R_6$, —$(C_2-C_6)$alkenyl-$R_6$, —$(C_2-C_6)$alkynyl-$R_6$, where $R_6$ represents aryl, heteroaryl, $(C_3-C_8)$heterocyclyl, or $(C_3-C_{14})$cycloalkyl, —$CH_2(CHOR_6)CH_2$—$OR_7$, where $R_7$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_6)$heterocyclyl, $(C_1-C_6)$alkyl-$(C_3-C_{14})$cycloalkyl,
or,
A'-CORM' where A' and CORM' are as defined respectively for A and CORM, and, when $R_1$ represents -Q'-Y, CORM represents a carbonyl metal complex chosen from among:
$Mn(CO)_5$,

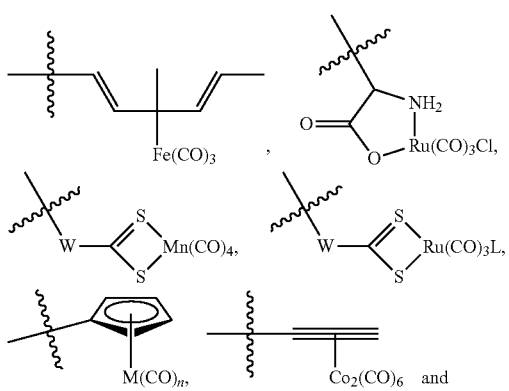

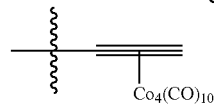

where W represents O or $NR_4$, where $R_4$ represents —$(C_1-C_6)$alkyl-,
L represents an ionic ligand such as halogen, or a counterion such as $BF_4$ or $PF_6$,
M represents Rh, Co, Ru, Mn, Mo, V or Fe, preferably Co, Ru or Mn and
n is an integer, chosen so that the metal M has no free valency;
and when $R_1$ represents A'-CORM', CORM represents a carbonyl metal complex chosen from among:
$Mn(CO)_5$,

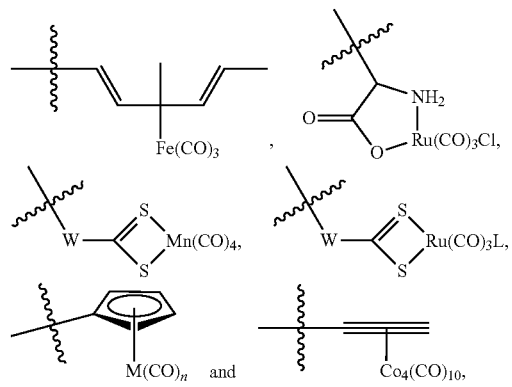

where W represents O or $NR_4$, where $R_4$ represents —$(C_1-C_6)$alkyl-,
L represents an ionic ligand such as halogen, or a counterion such as $BF_4$ or $PF_6$,
M represents Rh, Co, Ru, Mn, Mo, V or Fe, preferably Fe, Co, Ru or Mn and
n is an integer, chosen so that the metal M has no free valency;
preferably CORM represents a carbonyl metal complex chosen from among:
$Mn(CO)_5$,

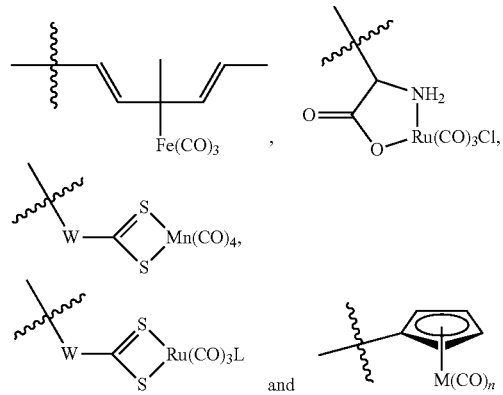

where W represents O or $NR_4$, where $R_4$ represents —$(C_1-C_6)$alkyl-,

L represents an ionic ligand such as halogen, or a counterion such as $BF_4$ or $PF_6$, M represents Rh, Ru, Mn, Mo, V or Fe, preferably Fe, Ru or Mn, and n is an integer, chosen so that the metal M has no free valency;

even more preferably CORM represents a carbonyl metal complex chosen from among:

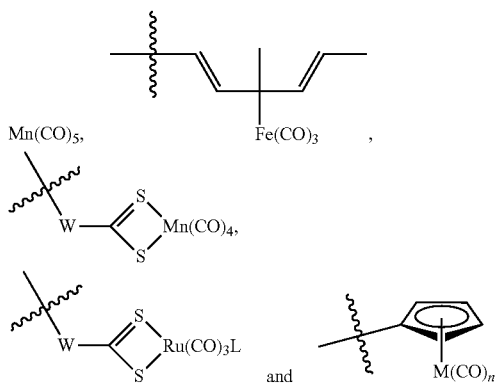

where W represents O or $NR_4$, where $R_4$ represents —$(C_1$-$C_6)$alkyl-,

L represents an ionic ligand such as halogen, or a counterion such as $BF_4$ or $PF_6$, M represents Fe or Mn, and n is an integer chosen so that the metal M has no free valency.

The present invention even more preferably relates to hybrid fumarate-carbon monoxide releasing molecules (fumarate-CORM), their pharmaceutically acceptable salts, hydrates and solvates, of formula (Ia):

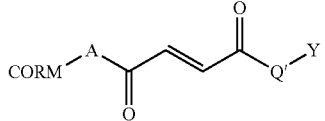

(Ia)

wherein A, CORM and -Q'-Y are as defined for formula (I).

In the case where CORM represents a carbonyl metal complex of formula:

M represents Rh, Co, Ru, Mn, Mo, V or Fe, preferably Co, Ru or Mn, and n is an integer chosen so that the metal M has no free valency, more preferably n is an integer from 1 to 4, chosen so that the metal M has no free valency. In particular, when M represents Rh, n represents 2; when M represents Co, n represents 2; when M represents Ru, n represents 2; when M represents Mn, n represents 3; when M represents Mo, n represents 3; when M represents V; n represents 4; when M represents Fe, n represents 3.

Advantageously, Q represents O or $NR_2$, preferably O and $R_2$ represents H or $(C_1$-$C_6)$alkyl.

Advantageously, Z represents —$(C_1$-$C_6)$alkyl-, —$(C_2$-$C_6)$alkenyl- or —$(C_3$-$C_8)$heterocyclyl-, —$(C_1$-$C_6)$alkyl-$R_3$—$(C_1$-$C_6)$alkyl-, —$(C_2$-$C_6)$alkenyl-$R_3$—$(C_1$-$C_6)$alkyl- and $R_3$ represents heteroaryl or $(C_3$-$C_8)$heterocyclyl.

Advantageously, Q represents O, S or $NR_2$, where $R_2$ represents H, $(C_1$-$C_6)$alkyl and Z represents —$(C_1$-$C_6)$alkyl-, —$(C_2$-$C_6)$alkenyl-, —$(C_3$-$C_6)$heterocyclyl-, —$(C_1$-$C_6)$alkyl-$R_3$—$(C_1$-$C_6)$alkyl-, —$(C_2$-$C_6)$alkenyl-$R_3$—$(C_1$-$C_6)$alkyl-, where $R_3$ represents heteroaryl or $(C_3$-$C_8)$heterocyclyl.

More advantageously, Z represents:

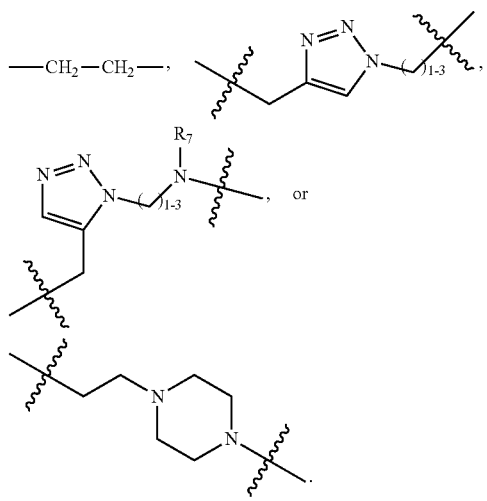

Advantageously, CORM is chosen from among:

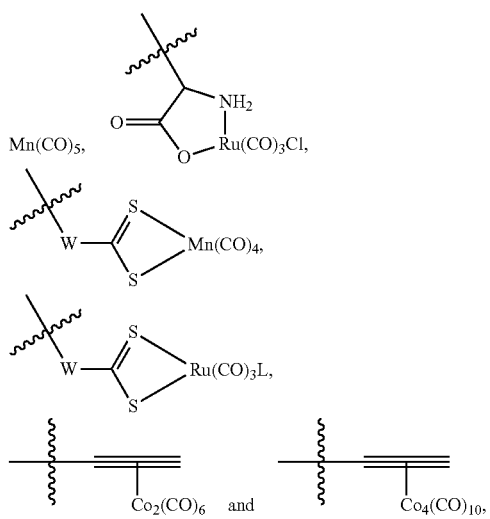

more advantageously from among

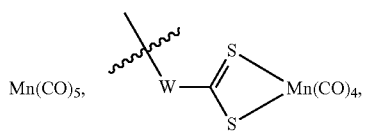

-continued

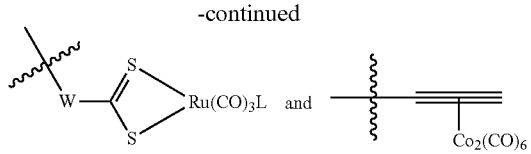

even more advantageously from among

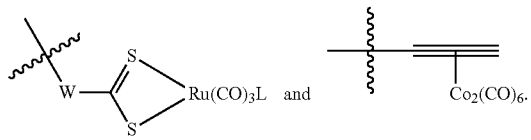

Advantageously, Q' is O or $NR_5$, preferably O.

Advantageously, Y is chosen from among H; —($C_1$-$C_6$)alkyl, —($C_2$-$C_6$)alkenyl; -aryl, -heteroaryl, —($C_2$-$C_6$)alkynyl, —($C_3$-$C_6$)heterocyclyl; —($C_3$-$C_8$)cycloalkyl or —($C_1$-$C_6$)alkyl-aryl.

According to a first embodiment, the invention concerns a hybrid fumarate-carbon monoxide releasing molecule (fumarate-CO—RM), in which the fumarate moiety is substituted on one side by a CO-releasing carbonyl complex and on the other side by an acid, an ester, a thioester or an amide, of formula (Ia):

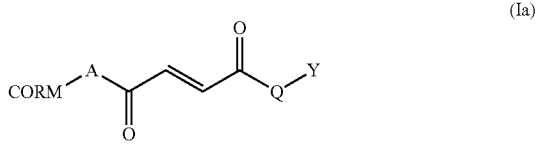

(Ia)

wherein A, CORM and -Q'-Y are as defined for formula (I).

Unexpectedly, it has been found that the compounds of formula (Ia) are capable of releasing CO at a fast rate. For example, compound A of the examples below, illustrative of the compounds of formula (Ia), is capable of releasing CO with a half-life of around 38 minutes under the in vitro conditions described in the examples, which is a fast rate in the sense of the present invention. The compounds of formula (Ia) are therefore advantageous for a relatively fast biological activity. Moreover, experiments demonstrate that the compounds of the invention comprising only one CORM group are potent activators of Nrf2 and inducers of HO-1 protein expression, and are more effective than dimethylfumarate.

Some advantageous compounds according to this first embodiment have formula (Ia1):

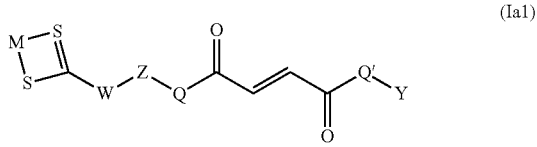

(Ia1)

wherein:

M represents $Mn(CO)_4$ or $Ru(CO)_3Cl$, and

Q, Q', W, Z and Y are as defined for formula (I).

Advantageously, in the compounds of formula (Ia1), Z—W is —$CH_2$—$CH_2$—$NR_7$—,

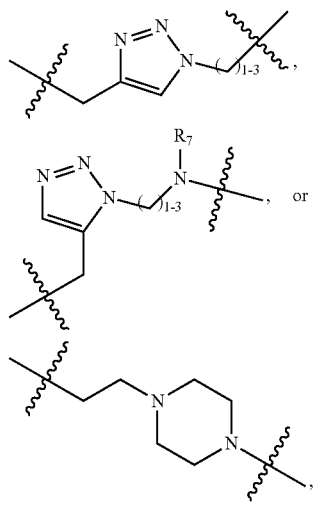

where $R_7$ represents ($C_1$-$C_3$)alkyl.

Advantageously, Q is O or $NR_2$, preferably O.

Advantageously, Q' is O or $NR_5$, preferably O.

Advantageously, Y represents H, —($C_1$-$C_6$)alkyl or —($C_2$-$C_6$)alkenyl.

Some other advantageous compounds according to this first embodiment have formula (Ia2):

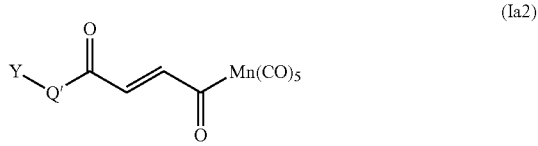

(Ia2)

wherein:

Q' and Y are as defined for formula (I).

Advantageously, Y is H, —($C_1$-$C_6$)alkyl or —($C_2$-$C_6$)alkenyl and Q' represents O.

Some further advantageous compounds according to this first embodiment have formula (Ia3):

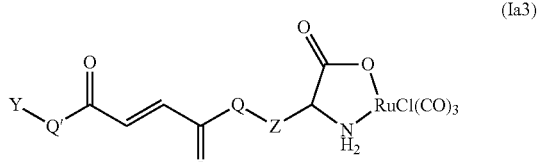

(Ia3)

wherein:

Q, Q', Y and Z are as defined for formula (I).

Advantageously, Y is H, —($C_1$-$C_6$)alkyl or —($C_2$-$C_6$)alkenyl, Q' is O, and Q and Z are as defined for formula (I). More advantageously, Q-Z is the side chain of an amino-acid such as serine, cysteine, tyrosine or lysine.

Further advantageous compounds according to this first embodiment have formula (Ia4):

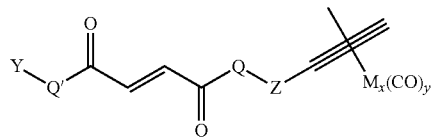
(Ia4)

wherein:
$M_x(CO)_y$ represents $Co_2(CO)_6$ or $Co_4(CO)_{10}$,
Q', Q, Y and Z are as defined for formula (I).

Advantageously, Y is H, —($C_1$-$C_6$)alkyl or —($C_2$-$C_6$) alkenyl, Q' is O, and Q and Z are as defined for formula (I).

More advantageously, Q is O and Z is —($C_1$-$C_6$)alkyl, preferably ($C_1$-$C_3$)alkyl.

In a second embodiment, the invention concerns a hybrid fumarate-carbon monoxide releasing molecule (fumarate-CO-RM) in which the fumarate moiety is substituted on both sides by a CO-releasing carbonyl complex.

These bimetallic compounds have been found to release a higher amount of CO compared to the monometallic over a long period of time and are therefore advantageous for a sustained biological activity over time. For example, compound B of the examples below, illustrative of the compounds of formula (Ic) described thereafter, is capable of releasing CO over 480 minutes under the in vitro conditions described in the examples, which is a long period of time in the sense of the present invention.

In some compounds according to this second embodiment, the hybrid fumarate-carbon monoxide releasing molecule is substituted on one side by one CO-releasing carbonyl complex and on the other side by a different CO-releasing carbonyl complex, according to formula (Ib):

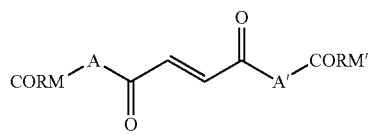
(Ib)

wherein A-CORM and A'-CORM' are as defined above or below for formula (I).

Advantageously, CORM and CORM' are respectively

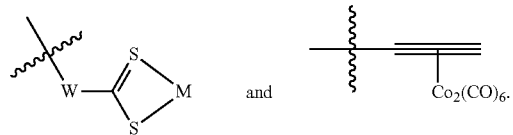

wherein M is $Mn(CO)_4$ or $Ru(CO)_3Cl$.

Advantageously, in the compounds of formula (Ib), A is Q-Z—W wherein Z—W is —$CH_2$—$CH_2$—$NR_7$—,

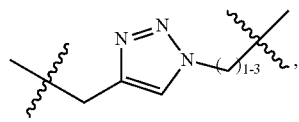

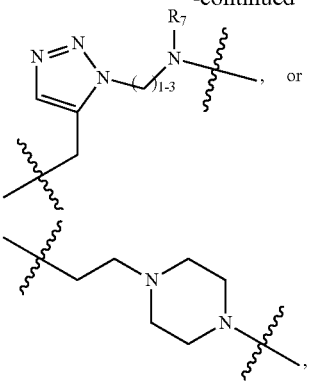

where $R_7$ represents ($C_1$-$C_3$)alkyl and A' is Q'-Z', wherein Z' is —($C_1$-$C_6$)alkyl, preferably ($C_1$-$C_3$)alkyl. Advantageously, Q is O or $NR_2$, preferably O and Q' is O or $NR_2$, preferably O.

Advantageously, the compounds according to the second embodiment have formula (Ic), wherein the fumarate moiety is substituted on both sides by the same CO-releasing carbonyl complex:

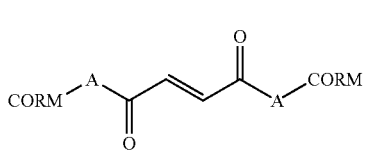
(Ic)

wherein A-CORM is as defined for the compounds of formula (I).

In this embodiment, CORM preferably represents a carbonyl metal complex chosen from among:
$Mn(CO)_5$,

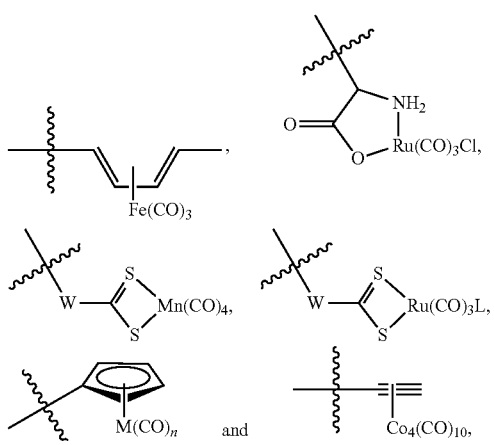

where W represents O or $NR_4$, where $R_4$ represents —($C_1$-$C_6$)alkyl-,
L represents an ionic ligand such as halogen, or a counter-ion such as $BF_4$ or $PF_6$,
M represents Rh, Co, Ru, Mn, Mo, V or Fe, preferably Fe, Co, Ru or Mn and
n is an integer chosen so that the metal M has no free valency;

preferably CORM represents a carbonyl metal complex chosen from among:
Mn(CO)$_5$,

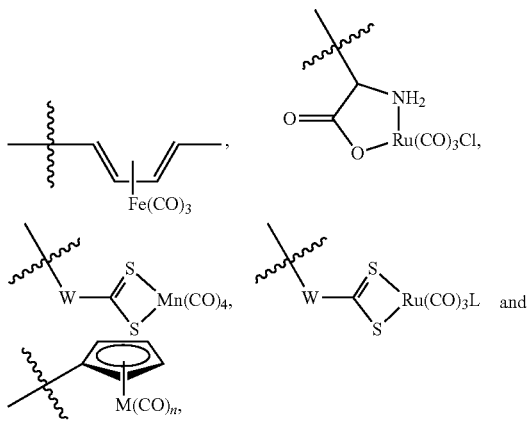

where W represents O or NR$_4$, where R$_4$ represents —(C$_1$-C$_6$)alkyl-,
L represents an ionic ligand such as halogen, or a counter-ion such as BF$_4$ or PF$_6$,
M represents Rh, Ru, Mn, Mo, V or Fe, preferably Fe, Ru or Mn, and
n is an integer chosen so that the metal M has no free valency;
even more preferably CORM represents a carbonyl metal complex chosen from among:
Mn(CO)$_5$,

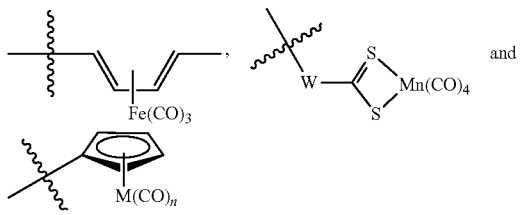

where W represents O or NR$_4$, where R$_4$ represents —(C$_1$-C$_6$)alkyl-,
L represents an ionic ligand such as halogen, or a counter-ion such as BF$_4$ or PF$_6$,
M represents Fe or Mn, and
n is an integer chosen so that the metal M has no free valency.

Some advantageous compounds of formula (Ic) have formula (Ic1):

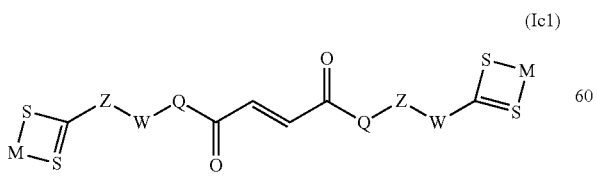

(Ic1)

wherein:
M represents Mn(CO)$_4$ or Ru(CO)$_3$Cl, and
Q and Z are as defined for formula (I).

Advantageously, in the compounds of formula (Ic1), Z—W is —CH$_2$—CH$_2$—NR$_7$—,

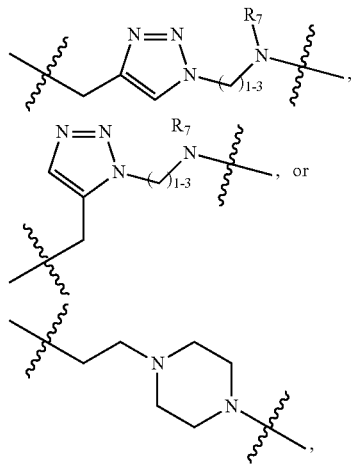

where R$_7$ represents (C$_1$-C$_3$)alkyl
Advantageously, Q is O or NR$_2$, preferably O.
Some other advantageous compounds of formula (Ic) have formula (Ic2):

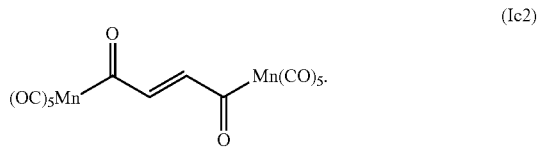

(Ic2)

Some further advantageous compounds of formula (Ic) have formula (Ic3):

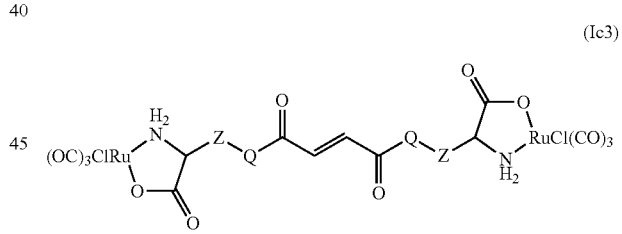

(Ic3)

wherein:
Q and Z are as defined for formula (I).
Advantageously, Q-Z is the side chain of an amino-acid such as serine, cysteine, tyrosine or lysine.
Further advantageous compounds of formula (Ic) have formula (Ic4):

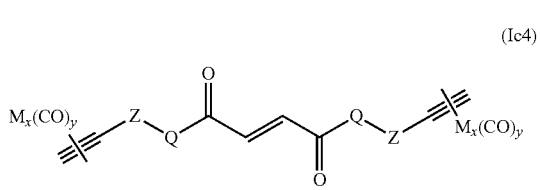

(Ic4)

wherein:

$M_x(CO)_y$ represents $Co_2(CO)_6$ or $Co_4(CO)_{10}$, preferably $Co_4(CO)_{10}$, Q and Z are as defined for formula (I).

More advantageously, Q is O and Z is —$(C_1$-$C_6)$alkyl, preferably $(C_1$-$C_3)$alkyl.

Advantageously, the compound of formula (I) is chosen from among:

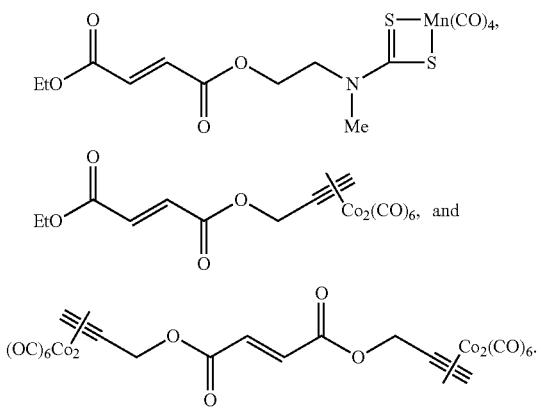

In a particular embodiment, the compound of formula (I) is:

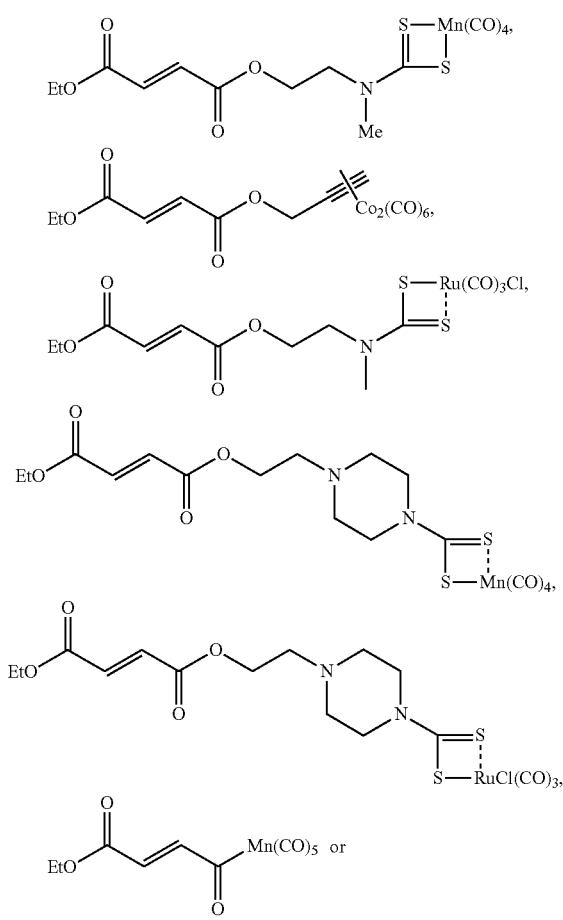

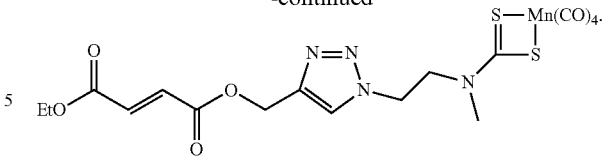

The invention also concerns a pharmaceutical composition comprising at least one compound of formula (I), a pharmaceutically acceptable salt, solvate or hydrate thereof, as defined previously and at least one pharmaceutically acceptable excipient.

The pharmaceutical compositions of the invention are advantageously suitable for administration via oral, sublingual, subcutaneous, intramuscular, intravenous, transdermal, topical or rectal route. The pharmaceutical compositions of the invention may also be administered by inhalation, for example by means of an aerosol. The active ingredient can be administered in unit forms for administration, mixed with conventional pharmaceutical carriers, to animals or to humans.

When a solid composition is prepared in the form of tablets, the main active ingredient is mixed with a pharmaceutical vehicle and other conventional excipients known to those skilled in the art.

The compounds of the invention can be used in a pharmaceutical composition at a dose ranging from 0.01 mg to 1000 mg a day, administered in only one dose once a day or in several doses along the day, for example twice a day. The daily administered dose is advantageously comprises between 5 mg and 500 mg, and more advantageously between 10 mg and 200 mg. However, it can be necessary to use doses out of these ranges, which could be noticed by the person skilled in the art.

The present invention further concerns a compound of formula (I), a pharmaceutically acceptable salt, solvate or hydrate thereof, or a pharmaceutical composition comprising at least one compound of formula (I), a salt, solvate or hydrate thereof, for use as a drug.

The present invention further concerns at least one compound of formula (I), a pharmaceutically acceptable salt, solvate or hydrate thereof, or a pharmaceutical composition comprising at least one compound of formula (I), a salt, solvate or hydrate thereof, for use in the treatment of cardiovascular or inflammatory diseases.

The present invention further concerns the use of at least one compound of formula (I), a pharmaceutically acceptable salt, solvate or hydrate thereof, for the manufacture of a medicament for use in the treatment of cardiovascular or inflammatory diseases.

The present invention further concerns a method for treating cardiovascular or inflammatory diseases, comprising the administration of at least one compound of formula (I), a pharmaceutically acceptable salt, solvate or hydrate thereof, or of a pharmaceutical composition comprising at least one compound of formula (I), a pharmaceutically acceptable salt, solvate or hydrate thereof, to a person in need thereof.

Inflammatory and cardiovascular diseases according to the present invention include for example myocardial ischemia and heart diseases, rheumatoid arthritis, acute and chronic skin wound (wound healing), inflammatory bowel disease, post-operative ileus, brain ischemia, psoriasis, diabetes, diabetic nephropathy, metabolic syndrome, sickle-cell disease, neurodegenerative diseases such as Alzheimer's disease or Parkinson's disease, neuropathic pain, hypertension, pulmonary arterial hypertension, septicemia, septic or endotoxic shock, hemorrhagic shock, multiple sclerosis, cancer and chronic obstructive pulmonary disease. Preferred inflammatory and cardiovascular diseases according to the present invention are skin wound (wound healing), brain and cardiac ischemia, psoriasis, diabetes, multiple sclerosis, cancer and chronic obstructive pulmonary disease. The present invention further concerns a process for preparing the compounds of formula (I), their salts, hydrates or solvates.

The compounds of formula (I) can be obtained according to two methods.

Method (a):

Step (1): The diacyl chloride, bromide, fluoride or di-activated ester of fumaric acid or the monoacyl chloride, bromide, fluoride or mono-activated ester of a mono-ester, mono-amide or mono-thioester of fumaric acid is esterified with a compound of formula (II) chosen from among:

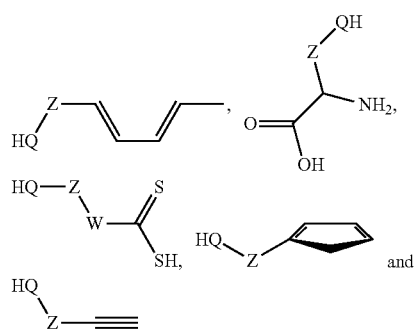

wherein Z and Q are as defined above.

Alternatively, fumaric acid or the mono-ester of fumaric acid may be alkylated with a compound of formula (III) chosen from among:

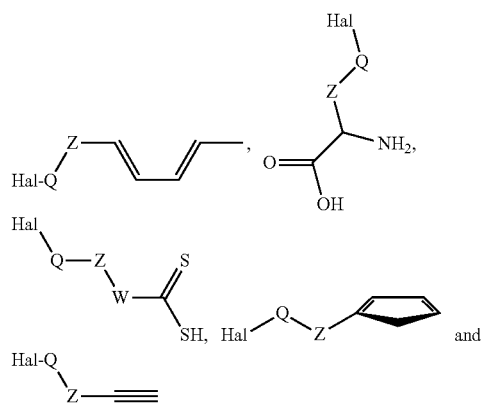

wherein Z and Q are as defined above and Hal represents a leaving group such as halogen or sulfonate, such as trifuoromethane-sulfonate.

Step (2): the compound obtained in step (1) is reacted with a suitable carbonyl metal complex of formula $L_1L_2M_x(CO)_y$, where x is 1 or 2 and y is 1 to 10, $L_1$ and $L_2$ represent each a monodentate ligand or $L_1L_2$ represents a bidentate ligand to yield after optional deprotection the compound of formula (I).

The invention therefore concerns a process for the synthesis of a compound of formula (I) comprising the reaction of a fumaric acid derivative of formula (IV):

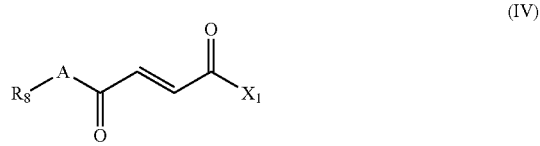

wherein:

$X_1$ represents A-$R_8$, A-CORM, A'-CORM' or Q'-Y as defined for formula (I), and $R_8$ represents a group chosen from among:

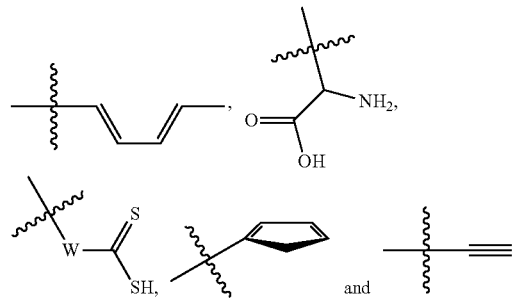

with a carbonyl metal complex of formula $L_1L_2M_x(CO)_y$, where x is 1 or 2 and y is 1 to 10, $L_1$ and $L_2$ represent each a monodentate ligand or $L_1L_2$ represents a bidentate ligand.

Method (b):

The diacyl chloride, bromide, fluoride or di-activated ester of fumaric acid or the monoacyl chloride, bromide, fluoride or mono-activated ester of a mono-ester, mono-amide or mono-thioester of fumaric acid is esterified with a compound of formula H-A-CORM. Alternatively, fumaric acid or the mono-ester of fumaric acid may be alkylated with a compound of formula Hal-A-CORM, wherein A is as defined above and Hal represents a leaving group such as halogen or sulfonate, such as trifuoromethane-sulfonate.

The invention therefore also concerns a process for the synthesis of a compound of formula (I) comprising the reaction of a fumaric acid derivative of formula (V):

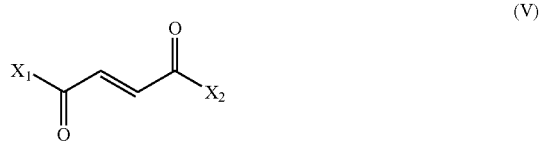

wherein:

$X_1$ represents Cl, F, Br or an ester, advantageously an activated ester, $X_2$ represents Cl, F, Br or an ester, advantageously an activated ester, A-CORM, A'-CORM' or Q'-Y as defined for formula (I), with a compound of formula H-A-CORM wherein A-CORM is as defined for formula (I), or, the reaction of a compound of formula (I) wherein $X_1$ and/or $X_2$ represent OH with a compound of formula Hal-A-CORM where Hal represents a leaving group, such as halogen or sulfonate, for example a trifluoromethane-sulfonate.

In the sense of the present invention, the term "leaving group" refers to a chemical group which can be easily replaced with a nucleophile during a nucleophile substitution reaction.

In the sense of the present invention, the expression "activated ester" is intended to designate an ester that enhances the reactivity of the carbonyl group(s) of fumaric acid. Such activated esters can be prepared before the reaction or generated in situ according to well-known procedures.

Examples of reagents usable for preparing the activated esters include coupling agents, such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), hexafluorophosphate 2H benzotriazole-1-yl)-1,1,3,3-tetramethyluronium (HBTU), tetrafluoroborate 2-(IH-benzotriazole-1-yl)-1,1,3,3-tetramethyluronium (TBTU), hexafluorophosphate O (7-azobenzotriazol-1-yl)-1,1,3,3-tetramethyluronium (HATU) or (benzotriazol-1-yloxy)tripyrrolodinophosphonium hexafluorophosphate (PyBOP); optionally associated with an auxiliary coupling, such as N-hydroxy-succinimide (NHS), N-hydroxy-benzotriazole (HOBt), 3,4-dihydro-3-hydroxy-4-oxo-1,2,3-benzotriazole (HOOBt), I-hydroxy-7-azabenzotriazole (HAt) or N-hydroxysylfosuccinimide (sulfo NHS).

When present, functional groups liable to interfere with the desired reaction, for example heteroatoms, such as N or O, may be protected to avoid undesirable reactions during synthetic procedures.

The person skilled in the art is liable to determine if protecting groups are necessary. Suitable protecting groups are known in the art and are for example disclosed in Greene, "Protective Groups In Organic synthesis", (John Wiley & Sons, New York (1981).

The monoesters of fumaric acid, that is, the compounds of formula (II), wherein $X_1$ represents Q'-Y, can be prepared by esterification, amidation or thioesterification of fumaric acid or a derivative thereof with a compound of formula H-Q'-Y, or by alkylation of fumaric acid with a compound of formula Hal-Y, wherein Hal is a leaving group such as Br, Cl, I or $OSO_2CF_3$ and Y is as defined above under conventional conditions.

The compounds of formula (V) wherein $X_1$ represents A-CORM can be prepared by reacting fumaric acid with a compound of formula H-A-CORM or Hal-A-CORM according to method (b) described above, and if required transformation of the carboxylic acid into an acyl chloride, bromide, fluoride or activated ester.

The compounds of formula (Ic) can be obtained in a one-step procedure by reacting the diacyl chloride of fumaric acid with two equivalents of a compound of formula H-A-CORM or two equivalents of a compound chosen from among:

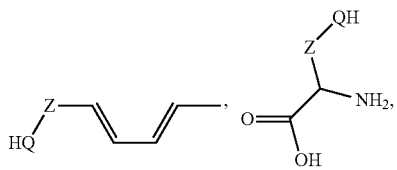

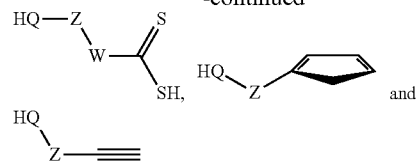

followed by the reaction with at least two equivalents of a carbonyl metal complex of formula $L_1L_2M_x(CO)_y$ where x is 1 or 2 and y is 1 to 10, $L_1$ and $L_2$ represent each a monodentate ligand or $L_1L_2$ represents a bidentate ligand with respect to the amount of the fumarate ester.

The compound of formula (Ia2) and (Ic2) can be obtained by reacting the monoacyl chloride of a fumarate ester or the diacyl chloride of fumaric acid with an appropriate amount of an anionic manganese carbonyl complex such as $Na^+[Mn(CO)_5]^-$.

The conditions for preparing the compounds of formula H-A-CORM or the compounds of formula (I) according to method (a) involve methods and procedures known in the art.

Definitions

The present invention encompasses only stable compounds. In this regard, when "isomers" are referred to, only stable isomers are considered.

Within the groups, radicals or fragments defined in the description and the claims, the number of carbon atoms is specified inside the brackets. For example, $(C_1-C_6)$alkyl designates an alkyl group or radical having 1 to 6 carbon atoms.

In the formulas, ⌇ indicates the bond linked to the rest of the molecule.

For the groups comprising two or more subgroups, the attachment is indicated with "—". For example, "—$(C_1-C_6)$alkyl-aryl-$(C_1-C_6)$alkenyl-" indicates a radical alkyl bound to a radical aryl itself bound to an alkenyl wherein the alkyl and alkenyl groups are bound to the rest of the molecule.

In the sense of the present invention, the expression "—$(C_1-C_6)$alkyl" designates an acyclic, saturated, linear or branched hydrocarbon chain comprising 1 to 6 carbon atoms. Examples of —$(C_1-C_6)$alkyl groups include methyl, ethyl, propyl, butyl, pentyl or hexyl. Unless explicitly stated, the definitions propyl, butyl, pentyl and hexyl include all possible isomers, in particular structural isomers. For example, butyl comprises n-butyl, iso-butyl, sec-butyl and tert-butyl.

In the sense of the present invention, the expression "—$(C_2-C_6)$alkenyl" designates an acyclic, saturated, linear or branched hydrocarbon chain comprising 2 to 6 carbon atoms, at least two of which are linked via a double bond. Examples of "—$(C_2-C_6)$alkenyl" include ethenyl or vinyl, propenyl, butenyl, pentenyl or hexenyl. Unless explicitly stated, the definitions of propenyl, butenyl, pentenyl and hexenyl include all possible isomers, in particular structural and/or position isomers.

In the sense of the present invention, the expression "—$(C_2-C_6)$alkynyl" designates an acyclic, saturated, linear or branched hydrocarbon chain comprising 2 to 6 carbon atoms, at least two of which are linked via a triple bond. Examples of "—$(C_2-C_6)$alkynyl" include ethynyl, propynyl, butynyl, pentynyl or hexynyl. Unless explicitly stated, the definitions of propynyl, butynyl, pentynyl and hexynyl include all possible isomers, in particular structural and/or position isomers.

The term substituted as used herein means that any of the hydrogen atoms can be replaced by a substituent, such as fluorine.

In the sense of the present invention, the expression "—($C_3$-$C_{14}$)cycloalkyl" designates a saturated or partially saturated mono-, di- or tri-cyclic structure comprising from 3 to 14 carbon atoms. Examples of "—($C_3$-$C_{14}$)cycloalkyl" include cyclopropyl, cyclobutyl, cyclopentyl, cyclohexyl, cycloheptyl, cyclooctyl, cyclopentenyl and cyclohexenyl.

Examples of "—($C_3$-$C_8$)cycloalkyl" include cyclopropyl, cyclobutyl, cyclopentyl, cyclohexyl, cycloheptyl or cyclooctyl. Unless explicitly stated, the cycloalkyls can be substituted by one or more groups such as methyl, ethyl, isopropyl, hydroxy, fluoro, chloro, bromo and iodo.

In the sense of the present invention, the expression "—($C_3$-$C_8$)heterocyclyl" designates saturated heterocycles having 3, 4, 5, 6, 7 or 8 atoms in the ring where 1, 2 or 3 heteroatoms chosen from among N, O and S replace the corresponding number of carbon atoms. Examples of "—($C_3$-$C_6$)heterocyclyl" include aziridinyl, oxyranyl, pyrrolidinyl, tetrahydrofuranyl, oxazolyl, piperidinyl, piperazinyl and morpholinyl.

The term "aryl" designates an aromatic, monocyclic ring that may be fused with a second saturated, unsaturated or aromatic ring. The term aryl include, without restriction to the following examples, phenyl, indanyl, indenyl, naphtyl, anthracenyl, phenanthrenyl, tetrahydronaphtyl and dihydronaphtyl. The most preferred aryl are those comprising one six-membered aromatic ring. The aryl group may be substituted, preferably with one or more groups independently selected from the group consisting of alkyl, alkoxy, halogen, hydroxyl, amino, nitro, cyano, trifluoro, carboxylic acid or carboxylic ester.

The term heteroaryl designates a mono- or polycyclic aryl as defined above where one or more carbon atoms have been replaced with one or more heteroatoms chosen from among N, O and S. Unless explicitly stated, the term "heteroaryl" includes all possible isomers, in particular position isomers.

Examples of heteroaryl groups include furyl, thienyl, imidazolyl, pyridyl, pyrrolyl, N-alkyl pyrrolyl, pyrimidinyl, pyrazinyl, tetrazolyl, triazolyl and triazinyl. The heteroaryl group may be substituted, preferably with one or more groups independently selected from the group consisting of alkyl, alkoxy, halogen, hydroxyl, amino, nitro, cyano, trifluoro, carboxylic acid or carboxylic ester. Preferred heteroaryls are those having 5 or 6 atoms in the ring, such as indolyl, pyrrolyl, pyridinyl, pyrrazolyl, triazolyl, furanyl or thienyl.

As used, herein, the term "halogen" designates a fluorine, chlorine, bromine or iodine atom.

For the purpose of the invention, the term "pharmaceutically acceptable" is intended to mean what is useful to the preparation of a pharmaceutical composition, and what is generally safe and non-toxic, for a pharmaceutical use.

The term <<pharmaceutically acceptable salt, hydrate of solvate>> is intended to mean, in the framework of the present invention, a salt of a compound which is pharmaceutically acceptable, as defined above, and which possesses the pharmacological activity of the corresponding compound. Such salts comprise:

(1) hydrates and solvates;

(2) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (3) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

DESCRIPTION OF THE FIGURES

FIG. 2 represents heme oxygenase activity in BV2 microglia in the absence (CON) or in the presence of increasing concentrations of compound A (FIG. 2A), or compound C, comparative compound CORM-401 of WO 2008/003953 and comparative compound J (FIG. 2B). Heme oxygenase activity is expressed on the Y axis as percentage of control.

FIG. 5 represents Nrf-2 expression (FIG. 5A) in BV2 microglia (control), in BV2 microglia in the presence of compound A and in BV2 microglia in the presence of compound B. The presence of the compound in the experiment is indicated by "+" and its absence by "−". FIG. 5B represents HO-1 expression in BV2 microglia in the absence (control) or in the presence of increasing concentration of compound A. FIG. 5C represents HO-1 expression and Nrf-2 expression in BV2 microglia in the presence of increasing concentration of compound C, comparative compound CORM-401 of WO 2008/003953 or comparative compound J.

Figure 1:
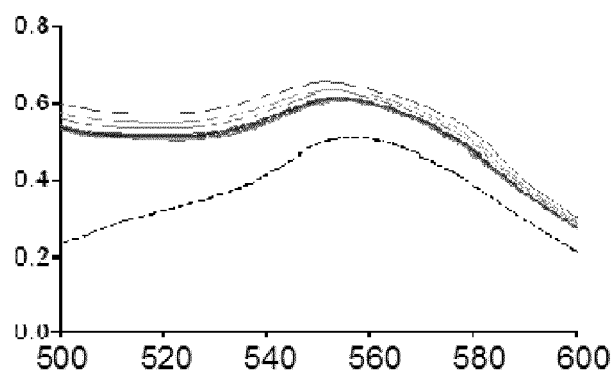
FIG. 1 represents the UV absorbance of carbon monoxy myoglobin (MbCO) in the presence of a curcumin derivative according to WO 2012/076696 (FIG. 1A), compound A (FIG. 1B) and compound B (FIG. 1C) at different times, The presence of absorbance peaks at 540 and 578 nm indicates the formation of carbon monoxy myoglobin (MbCO) (FIG. 1A-C). The intracellular CO according to the COP-1 assay of example 2 for different concentrations of Compound C is found in FIG. 1D.
Figure 1:
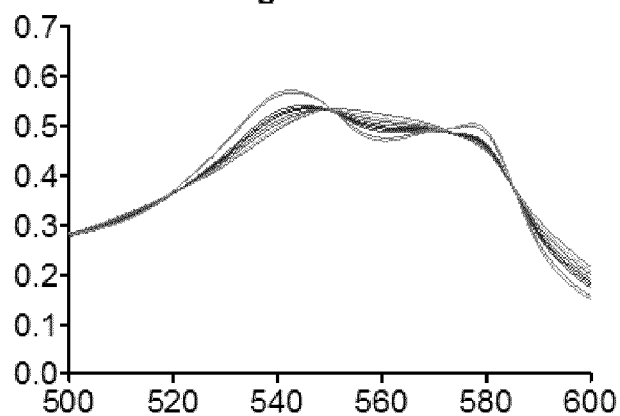
Figure 1:
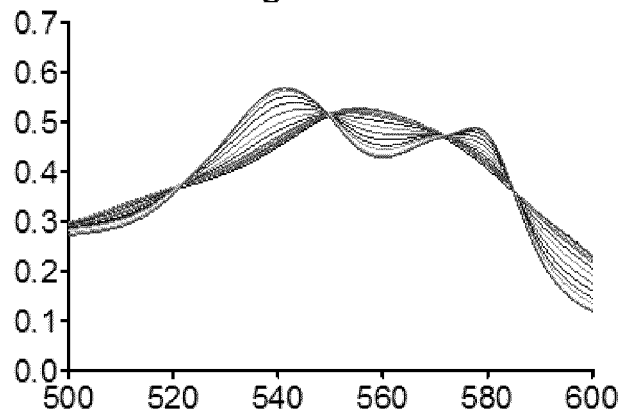

The present invention is illustrated by the non-limiting following examples.

EXAMPLES

Example 1: Synthesis of Hybrids Fumarate-CO-RM According to the Invention

Compound A:

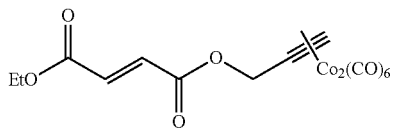

Step 1: Preparation of:

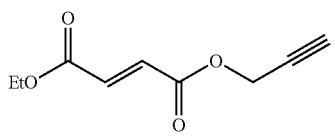

A solution of mono-ethyl fumarate (1.544 g, 10.78 mmol), propargyl bromide (4.488 g, 37.73 mmol) and potassium carbonate (1.851 g, 13.34 mmol) in acetone (104 mL) is stirred at room temperature for 48 hours. The formed potassium bromide is filtered off and the solvent removed under reduced pressure. The crude mixture is purified by flash chromatography on silica gel, eluting with Cyclohexane/ethyl acetate (8/2 Rf=0.5) to afford the expected product in 68% yield as a colorless liquid.

NMR (400 MHz) in CDCl$_3$:
$^1$H δ(ppm): 1.32 (t, 3H, CH$_3$, J=7.1 Hz); 2.52 (t, 1H, CH, J=0.1 Hz); 4.26 (q, 2H, CH$_2$, J=7.1 Hz); 4.8 (d, 2H, CH$_2$, J=2.4 Hz); 6.86 (d, 1H, CH=CH, J=15.8 Hz); 6.92 (d, 1H, CH=CH, J=15.8 Hz).
$^{13}$C δ(ppm): 14.2 (CH$_3$—CH$_2$); 52.8 (CH$_2$O); 61.6 (CH$_3$—CH$_2$); 75.6 (CH); 76.8 (C); 132.5 (CH=CH); 134.9 (CH=CH); 164.3 (C=O); 164.8 (C=O).

Elemental analysis: Calc.: C, 59.34; H, 5.53. Found: C, 59.13; H, 5.53.
MS (EI) m/z: [M+H]$^+$=183 (17); 137 (25.44); 127 (100); 99.1 (29.44); 81.1 (17.05); 79.1 (24.25); 71.1 (17.94); 55 (48.89); 53.1 (31.65).
IR (ATR, cm$^{-1}$): 3300, 1663, 1617.

Step 2: Preparation of Compound A

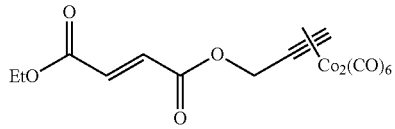

In a schlenk tube protected from light and under inert atmosphere of argon, a solution of the fumarate obtained in step 1 (0.1012 g, 0.5560 mmol, 1 eq.), of dicobalt octacarbonyl (CO$_2$(CO)$_8$, 0.1901 g, 0.5560 mmol, 1 eq.) in anhydrous diethyl ether (2 mL) is stirred at room temperature for 3 h40 (reaction completion is monitored by TLC). The solvent is removed under reduced pressure and with exclusion of light. The crude mixture is taken up in cyclohexane (15 mL) and the precipitated KBr is filtered onto celite. After evaporation of cyclohexane, an oily purple-black residue is obtained and purified by preparative chromatography on alumina (eluent: pentane/diethyl ether: 9/1).

187.4 mg of an oily compound are obtained. Recrystallization of 101 mg of the oil in hexane at −18° C. afforded 70 mg of compound A as red-black crystals.

NMR (400 MHz) in CDCl$_3$
$^1$H δ(ppm): 1.26 (s, 3H, CH$_3$); 4.19 (s, 2H, CH$_2$O); 5.35 (s, 2H, CH$_2$); 6.02 (s, 1H, CH); 6.85 (s, 2H, CH=CH).
$^{13}$C δ(ppm): 13.1 (CH$_3$—CH$_2$); 60.4 (OCH$_2$); 64.8 (CH$_3$—CH$_2$); 70.9 (CH); 86.7 (C); 131.6 (CH=CH); 133.6 (CH=CH); 163.3 (C=O); 163.8 (C=O); 197.9 (C=O).

Elemental analysis: Calc.: C, 38.49; H, 2.15. Found: C, 38.45; H, 2.25.
IR (ATR, cm$^{-1}$): 2100, 2050 (CO); 1967 (CO); 1717.

Compound B:

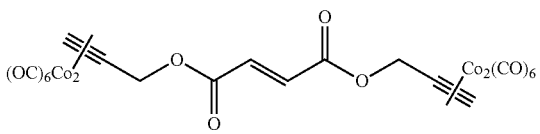

Step 1: Preparation of:

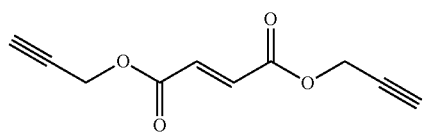

In a Schlenk tube, 0.1 g (1 eq, 7.10$^{-4}$ mol) of potassium carbonate and 0.275 g (2 eq, 1.4 10$^{-3}$ mol) of tetraethylammonium bromide (Et$_4$NBr) dissolved in 10 mL of chloroform, are successively added 76 µl (1 eq, 7.10$^{-4}$ mol) of fumaryl chloride and 82 µl (2 eq, 1.4 10$^{-3}$ mol) of propargyl alcohol. The solution is then stirred at room temperature overnight.

The solvent is removed under reduced pressure and the product is obtained after flash chromatography on silica gel (eluent: 8/2 cyclohexane/ethyl acetate) as a white solid in 50% yield.

¹H NMR (CDCl₃): 2.46 (2H, 3 Hz, t, H1), 4.74 (4H, 3 Hz, t, H3), 6.87 (2H, s, H5)

¹³C NMR (CDCl₃): 75.6 (C3), 133.7 (C5), 163.8 (C4)

IR:ν=1650, 1720 cm⁻¹

Step 2: Preparation of Compound B

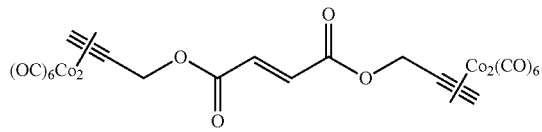

200 mg (1.04 10⁻³ mol) of the fumarate obtained in step 1 are dissolved in 10 ml of chloroform in a Schlenk tube protected from light. A solution of dicobalt octacarbonyl in chloroform is added dropwise at room temperature (356 mg, 1.04 10⁻³ mol in 15 ml of chloroform) and the reaction progress is monitored by TLC. After completion of the reaction, chloroform is removed under pressure and the product is obtained after silica gel chromatography (eluent 6/4 cyclohexane/chloroform) as a red-black powder.

¹H NMR (CDCl₃): 6.95 (1H, H5), 6.04 (1H, H1), 5.40 (2H, H3)

¹³C NMR (CDCl₃): 199 (12C, C6), 164.6 (2C, C4), 133, (2C, C5), 87.9 (2C, C2), 72 (2C, C1), 66.2 (2C, C3)

Elemental analysis: Calc.: C, 34.58; H, 1.06; Found: C, 34.99; H, 1.30.

IR:ν=2097, 2013, 1714 cm⁻¹

Compound C:

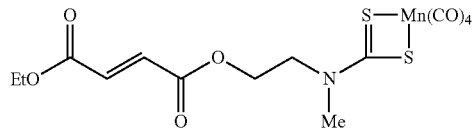

Step 1: Preparation of Sodium (2-hydroxyethyl)(methyl) carbamodithioate

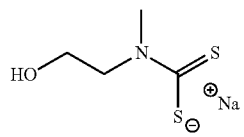

To a solution of carbon disulfide (452 μL, 7.5 mmol, 1.5 eq.) in 10 mL anhydrous THF under intert atomsphere of argon, is added dropwise at 0° C., 2-(methylamino)ethanol (400 μL, 5.0 mmol, 1.0 eq.). After stirring at 0° C. for 5 minutes, sodium hydride (60% dispersion in mineral oil, 200 mg, 5.0 mmol, 1.0 eq.) is added in portions. After 30 minutes of stirring at 0° C., the mixture is concentrated under reduced pressure and washed with cyclohexane to remove mineral oil and dried overnight under reduced pressure to yield a pale yellow powder (842 mg, 4.9 mmol, 97% yield).

¹H NMR (400 MHz, MeOD) δ (ppm): 3.57 (s, 3H, CH₃), 3.87 (t, J=6 Hz, 2H, CH₂N), 4.27 (t, J=6 Hz, 2H, CH₂O)

¹³C NMR (100 MHz, MeOD) δ (ppm): 44.7 (CH₃N), 59.1 (CH₂N), 61.2 (CH₂O), 214.0 (CS₂).

Step 2: Preparation of

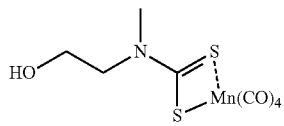

To a solution of Mn(CO)₅Br (137 mg, 0.50 mmol, 1.0 eq., prepared according to US 2010/0105770) in argon-flushed methanol (8 mL) is added sodium (2-hydroxyethyl)(methyl) carbamodithioate prepared in step 1 (87 mg, 0.50 mmol, 1.0 eq.). after 3 h30 of stirring at 45° C. under inert atmosphere of argon, the mixture is taken up in diethyl ether, filtered over celite and concentrated to afford a yellow oil (149 mg, 0.47 mmol, 94% yield) that is used without further purification in step 3.

¹H NMR (400 MHz, CDCl₃) δ (ppm): 3.34 (s, 3H, CH₃N), 3.48 (s, 1H, OH), 3.92 (s, 4H, CH₂N, CH₂O)

¹³C NMR (100 MHz, CDCl₃) δ (ppm): 38.5 (CH₃N), 53.4 (CH₂N), 60.3 (CH₂O), 198.7 (CS₂), 208.9 (CO)

⁵⁵Mn NMR (100 MHz, CDCl₃) δ (ppm): −993.1

Step 3: Preparation of Compound C

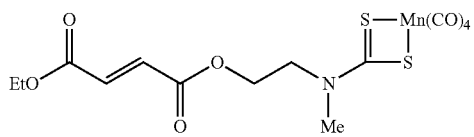

To a solution of the compound obtained in step 2 (149 mg, 0.47 mmol, 1.0 eq.) in anhydrous dichloromethane (10 mL) are added under inert atmosphere of argon, (E)-Ethyl-4-chloro-4-oxobut-2-enoate (115 mg, 0.71 mmol, 1.5 eq., prepared as described in J. Am. Chem. Soc., 1996, 118, 8266-8277) and triethylamine (99 μL, 0.71 mmol, 1.5 eq.). After stirring at 20° C. under argon for 18 hours, the mixture is concentrated under reduced pressure. The crude mixture is taken up in diethyl ether and filtered over celite. After evaporation of the solvent and flash chromatography on silica gel, (eluent: ethyl acetate/cyclohexane: 3/7+0.1% NEt₃), 107 mg of a yellow solid are obtained (0.24 mmol, 51% yield).

¹H NMR (400 MHz, CDCl₃) δ (ppm): 1.33 (s, 3H, CH₃C), 3.30 (s, 3H, CH₃N), 4.05 (s, 2H, CH₂N), 4.27 (s, 2H, CH₂O), 4.46 (s, 2H, CH₂O), 6.87 (s, 1H, CH═C), 6.88 (s, 1H, CH═C)

¹³C NMR (100 MHz, CDCl₃) δ (ppm): 14.1 (CH₃C), 37.8 (CH₃N), 49.8 (CH₂N), 61.4 (CH₂O), 61.5 (CH₂O), 132.4 (CH═O), 134.9 (CH═O), 164.6 (CO$_{ester}$), 164.7 (CO$_{ester}$), 197.0 (CS₂), 210.1 (CO$_{metal}$)

⁵⁵Mn NMR (100 MHz, CDCl₃) δ (ppm): −984.5

Elemental analysis: Calc. C (37.93), H (3.18), N (3.16); Found C (38.12), H (3.28), N (3.09).

Compound D:

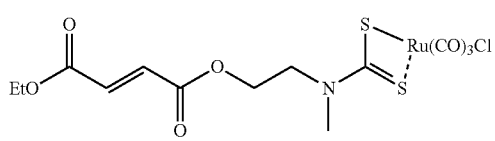

Step 1: Preparation of Compound AO234

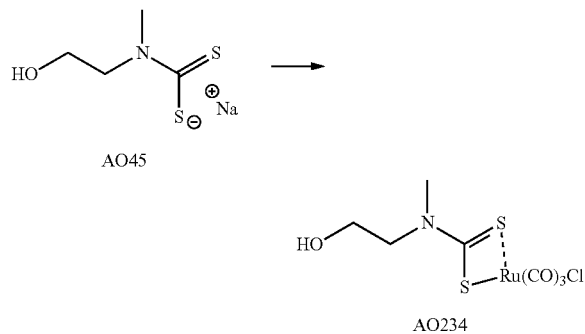

To a suspension of [RuCl$_2$(CO)$_3$]$_2$ (324 mg, 0.63 mmol, 0.5 equiv.) in methanol (13 mL) was added sodium (2-hydroxyethyl)(methyl)carbamodithioate (prepared as in step 1 of the synthesis of compound C) (219 mg, 1.26 mmol, 1.0 equiv.). After 3 h of stirring at 20° C. under argon, the reaction mixture was concentrated in vacuo, dissolved in EtOAc, filtered on celite and concentrated in vacuo to afford compound AO234 (435 mg, 1.17 mmol) as a yellow pale solid which was used in the next step without further purification. $^1$H NMR (400 MHz, MeOD) δ 3.96-3.77 (M, 4H, CH$_2$N, CH$_2$O), 3.37 (s, 3H, CH$_3$N). $^{13}$C NMR (100 MHz, MeOD) δ 210.27 (CS$_2$), 188.95 (CO$_{metal}$), 188.72 (CO$_{metal}$), 59.81 (CH$_2$O), 55.03 (CH$_2$N), 38.86 (CH$_3$N).

Step 2: Preparation of Compound D

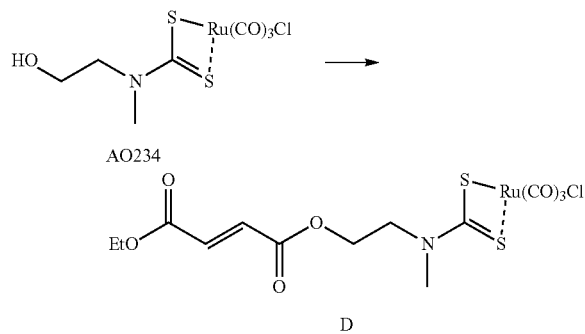

To a solution of compound AO234 (435 mg, 1.17 mmol, 1.0 equiv.) in anhydrous dichloromethane (16 mL) were added under argon (E)-4-chloro-4-oxo-2-butenoic acid ethyl ester (285 mg, 1.76 mmol, 1.5 equiv.) and 4-DMAP (215 mg, 1.76 mmol, 1.5 equiv.). After 17 h of stirring at 40° C. under argon, the reaction mixture was concentrated in vacuo. The resulting crude product was purified by silica gel column chromatography eluting with cyclohexane/EtOAc (60/40) and dried with a vane pump during one night to afford compound D (312 mg, 0.63 mmol) as a white solid in 50% yield (two steps). $^1$H NMR (400 MHz, CDCl$_3$) δ 6.89 (d, J=21.2 Hz, 1H, CH═C), 6.85 (d, J=21.2 Hz, 1H, CH═C), 4.48 (m, 2H, CH$_2$O), 4.30 (m, 1H, CH$_2$N), 4.26 (q, J=7.2 Hz, 2H, CH$_2$O), 3.80 (m, 1H, CH$_2$N), 3.35 (s, 3H, CH$_3$N), 1.32 (t, J=7.2 Hz, 3H, CH$_3$C). $^{13}$C NMR (100 MHz, CDCl$_3$) δ 211.09 (CS$_2$), 186.98 (CO$_{metal}$), 186.67 (CO$_{metal}$), 186.66 (CO$_{metal}$), 164.59 (CO$_{ester}$), 164.47 (CO$_{ester}$), 135.07 (CH═C), 132.17 (CH═C), 61.51 (CH$_2$O), 61.13 (CH$_2$O), 50.09 (CH$_2$N), 37.92 (CH$_3$N), 14.05 (CH$_3$C). Anal. Calcd for C$_{13}$H$_{14}$ClNO$_7$RuS$_2$ (496.91): C, 31.42; H, 2.84; N, 2.82. Found: C, 31.49; H, 2.80; N, 2.79.

Compound E:

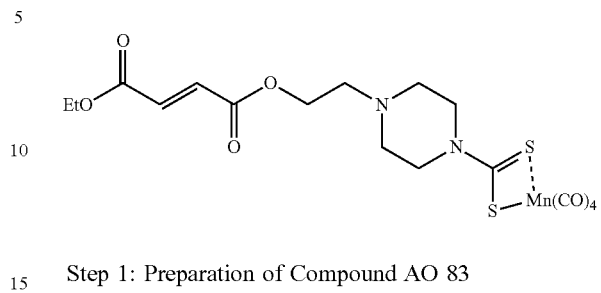

Step 1: Preparation of Compound AO 83

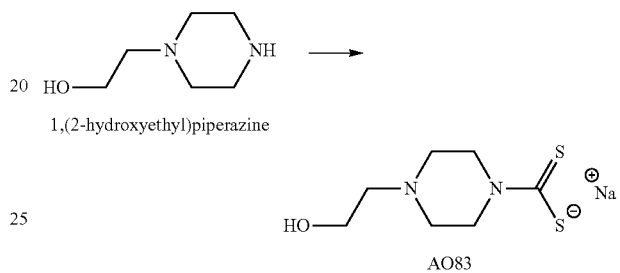

To a solution of 1-(2-hydroxyethyl)piperazine (651 mg, 5.00 mmol, 1.0 equiv.) in anhydrous tetrahydrofuran (15 mL) was added, at 0° C. under argon and dropwise, carbon disulfide (452 μL, 7.50 mmol, 1.5 equiv.). After 15 min of stirring at 0° C., sodium hydride (60% dispersion in mineral oil) (200 mg, 5.00 mmol, 1.0 equiv.) was added portionwise. After 40 min of stirring at 0° C., the reaction mixture was concentrated in vacuo. The resulting crude product was washed several times with cyclohexane to eliminate mineral oil and then concentrated in vacuo et dried with a vane pump during one night to afford compound AO83 (1.10 g, 4.82 mmol) as a pale yellow powder in 96% yield which was used in the next step without further purification. $^1$H NMR (400 MHz, MeOD) δ 4.46 (t, J=4.8 Hz, 4H, CH$_2$N), 3.71 (t, J=5.9 Hz, 2H, CH$_2$O), 2.55 (t, J=5.1 Hz, 6H, CH$_2$N). $^{13}$C NMR (100 MHz, MeOD) δ 60.98 (CH$_2$N), 59.80 (CH$_2$O), 54.35 (CH$_2$N), 51.20 (CH$_2$N).

Step 2: Preparation of Compound AO208

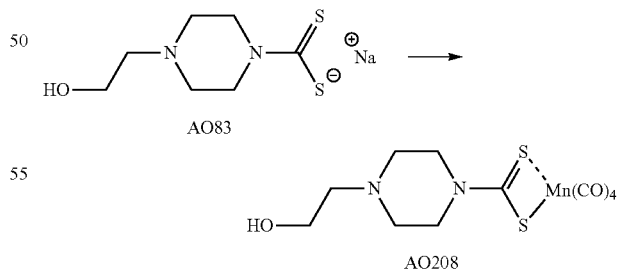

To a solution of compound AO83 (318 mg, 1.39 mmol, 1.1 equiv.) in methanol (20 mL) was added Mn(CO)$_5$Br (346 mg, 1.26 mmol, 1.0 equiv.). After 3 h of stirring at 45° C. under argon, the reaction mixture was concentrated in vacuo, dissolved in diethyl ether, filtered on celite and concentrated in vacuo to afford compound AO208 (443 mg, 0.32 mmol) as a yellow oil in 94% yield which was used in the next step without further purification. $^1$H NMR (400 MHz, MeOD) δ 3.91 (s, 4H, CH$_2$N), 3.68 (s, 2H, CH$_2$O), 2.58 (s, 6H, CH$_2$N). $^{13}$C NMR (100 MHz, MeOD) δ 207.67 (CO$_{metal}$), 60.60 (CH$_2$N), 59.79 (CH$_2$O), 53.34 (CH$_2$N), 46.86 (CH$_2$N). $^{55}$Mn NMR (100 MHz, MeOD) δ-1025.7. Anal. Calcd for C$_{11}$H$_{13}$MnN$_2$O$_5$S$_2$ (372.30): C, 35.49; H, 3.52; N, 7.52. Found: C, 35.64; H, 3.71; N, 7.10.

Step 3: Preparation of Compound E

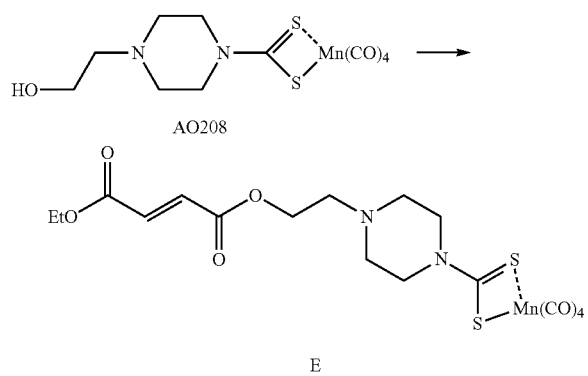

E

To a solution of compound AO208 (247 mg, 0.66 mmol, 1.0 equiv.) in anhydrous dichloromethane (9 mL) were added under argon (E)-4-chloro-4-oxo-2-butenoic acid ethyl ester (162 mg, 1.00 mmol, 1.5 equiv.) and 4-DMAP (122 mg, 1.00 mmol), 1.5 equiv.). After 18 h of stirring at 40° C. under argon, the reaction mixture was concentrated in vacuo, then, dissolved in diethyl ether, filtered on celite and concentrated in vacuo. The resulting crude product was purified by silica gel column chromatography eluting with cyclohexane/EtOAc (70/30+0.1% NEt$_3$) to afford compound E (151 mg, 0.30 mmol) as a yellow solid in 45% yield. $^1$H NMR (400 MHz, C$_6$D$_6$) δ 6.96 (s, 2H, CH$_2$=C), 3.88 (s, 2H, CH$_2$O), 3.79 (s, 2H, CH$_2$O), 3.23 (s, 4H, CH$_2$N), 1.87 (s, 2H, CH$_2$N), 1.65 (s, 4H, CH$_2$N), 0.86 (s, 3H, CH$_3$C). $^{13}$C NMR (100 MHz, C$_6$D$_6$) δ 206.93 (CO$_{metal}$) 164.55 (CO$_{ester}$), 134.27 (CH$_2$=C), 133.33 (CH$_2$=C), 61.82 (CH$_2$O), 61.23 (CH$_2$O), 55.78 (CH$_2$N), 51.54 (CH$_2$N), 45.87 (CH$_2$N), 13.95 (CH$_3$C). $^{55}$Mn NMR (100 MHz, C$_6$D$_6$) δ-990.3. Anal. Calcd for C$_{17}$H$_{19}$MnN$_2$O$_8$S$_2$ (498.41): C, 40.97; H, 3.84; N, 5.62. Found: C, 41.08; H, 4.06; N, 5.73.

Compound F:

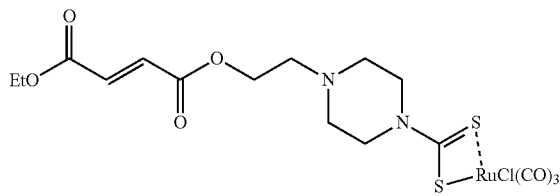

Step 1: Preparation of Compound AO228

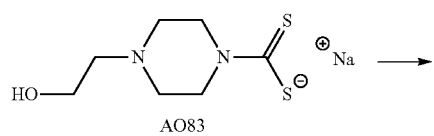

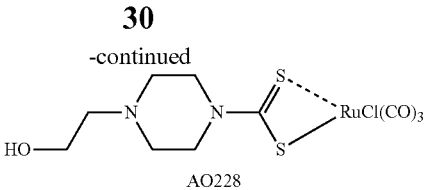

AO228

To a suspension of [RuCl$_2$(CO)$_3$]$_2$ (256 mg, 0.50 mmol, 0.5 equiv.) in methanol (10 mL) was added compound AO83 (228 mg, 1.00 mmol, 1.0 equiv.). After 4 h of stirring at 20° C. under argon, the reaction mixture was concentrated in vacuo, dissolved in EtOAc, filtered on celite and concentrated in vacuo to afford AO228 (370 mg, 0.87 mmol) as a yellow pale solid in 87% yield which was used in the next step without further purification. $^1$H NMR (400 MHz, MeOD) δ 3.96 (d, J=5.0 Hz, 4H, CH$_2$N), 3.72 (t, J=5.6 Hz, 2H, CH$_2$O), 2.76 (s, 4H, CH$_2$N), 2.68 (s, 2H, CH$_2$N). $^{13}$C NMR (100 MHz, MeOD) δ 188.76 (CO$_{metal}$) 188.59 (CO$_{metal}$), 60.50 (CH$_2$N), 59.41 (CH$_2$O), 52.98 (CH$_2$N), 47.00 (CH$_2$N).

Step 2: Preparation of Compound F

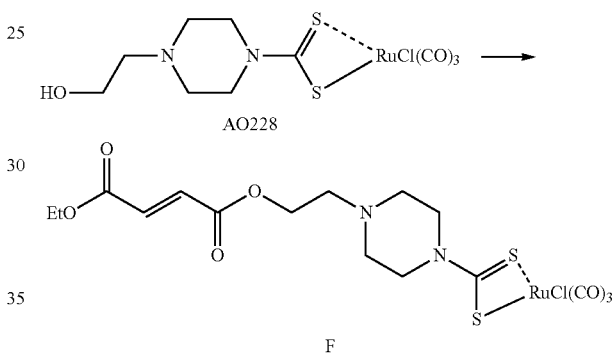

F

To a solution of compound AO228 (370 mg, 0.87 mmol, 1.0 equiv.) in anhydrous dichloromethane (11 mL) were added under argon (E)-4-chloro-4-oxo-2-butenoic acid ethyl ester (211 mg, 1.30 mmol, 1.5 equiv.) and 4-DMAP (159 mg, 1.30 mmol, 1.5 equiv.). After 16 h of stirring at 40° C. under argon, the reaction mixture was concentrated in vacuo, dissolved in EtOAc, filtered on celite and concentrated in vacuo The resulting crude product was purified by silica gel column chromatography eluting with cyclohexane/EtOAc (50/50) and dried with a vane pump during one night to afford Compound F (193 mg, 0.35 mmol) as a white solid in 40% yield. $^1$H NMR (400 MHz, CDCl$_3$) δ 6.87 (s, 2H), 4.34 (t, J=5.6 Hz, 2H), 4.27 (q, J=7.1 Hz, 2H), 3.88 (t, J=4.9 Hz, 4H), 2.75 (t, J=5.5 Hz, 2H), 2.65 (m, 4H), 1.33 (t, J=7.1 Hz, 3H). $^{13}$C NMR (100 MHz, CDCl$_3$) δ 186.78 (CO$_{metal}$), 164.82 (CO$_{ester}$), 134.26 (CH$_2$=C), 133.07 (CH$_2$=C), 62.09 (CH$_2$O), 61.47 (CH$_2$O), 56.06 (CH$_2$N), 51.88 (CH$_2$N), 46.48 (CH$_2$N), 14.11 (CH$_3$C). Anal. Calcd for C$_{16}$H$_{19}$ClN$_2$O$_7$RuS$_2$ (551.98): C, 34.81; H, 3.47; N, 5.08. Found: C, 35.04; H, 3.59; N, 4.91.

Compound G:

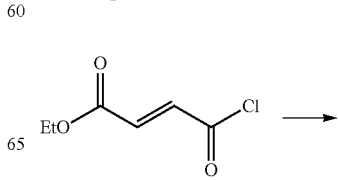

-continued

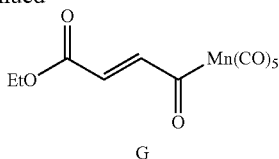

G

In a schlenk tube at 20° C. under argon, sodium (30 mg, 1.28 mmol, 2.8 equiv.) is added portionwise to mercury (240 µL) under vigorous stirring. After disappearance of sodium, anhydrous tetrahydrofuran (5 mL) is introduced, followed by addition of decacarbonyldimanganese (179 mg, 0.46 mmol, 1.0 equiv.). After 3 h of vigorously stirring at 20° C. and 10 min of decantation, the upper layer is transferred by cannula into another schlenk tube and cooled to −78° C. before (E)-4-chloro-4-oxo-2-butenoic acid ethyl ester (242 mg, 1.00 mmol, 2.2 equiv.) was added dropwise. After 1 h of stirring at −78° C. and 18 h of stirring at 20° C., the mixture is concentrated in a vacuo. The crude product is dissolved in hexane (6 mL), stirred during 30 min at 20° C., filtered on a frit glass and the filtrate is stored at −18° C. during 18 h for crystallizing. The crystallized solid is collected by removing the solvent and dried briefly with a vane pump to afford compound G (29 mg, 0.090 mmol) as an orange red solid in 5% yield. $^1$H NMR (400 MHz, $C_6D_6$) δ 7.40 (d, J=15.5 Hz, 1H), 5.87 (d, J=15.3 Hz, 1H), 3.90 (q, J=7.2 Hz, 2H), 0.87 (t, J=7.2 Hz, 3H). $^{55}$Mn NMR (100 MHz, $C_6D_6$) δ-1779.7. Anal. Calcd for $C_{11}H_7MnO_8$ (322.11): C, 41.02; H, 2.19. Found: C, 40.76; H, 2.50.

Compound I:

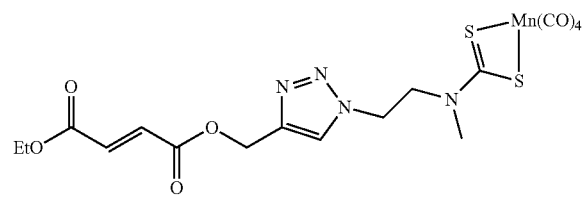

Step 1: Preparation of Compound AO219

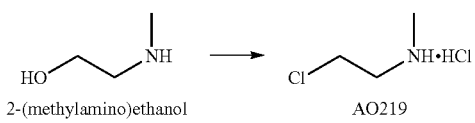

To a solution of 2-(methylamino)ethanol (400 µL, 5.00 mmol, 1.0 equiv.) in chloroform (50 mL) was added, under argon at 0° C., thionyle chloride (1.09 mL, 15.0 mmol, 3.0 equiv.). After 17 h of stirring at 50° C., the solvent was concentrated until approximately 10 mL, then diethyl ether (40 mL) was added to precipitate the compound which was collected on a frit glass, washed several times diethyl ether and dried with a vane pump during one night to afford compound AO219 (567 mg, 4.36 mmol) as a white solid in 87% yield which was used in the next step without further purification. $^1$H NMR (400 MHz, MeOD) δ 3.91 (t, J=5.4 Hz, 2H, $CH_2Cl$), 3.42 (t, J=5.4 Hz, 2H, $CH_2N$), 2.77 (s, 3H, $CH_3N$). $^{13}$C NMR (100 MHz, MeOD) δ 51.46 ($CH_2N$), 40.22 ($CH_2Cl$), 33.64 ($CH_3N$).

Step 2: Preparation of Compound AO220

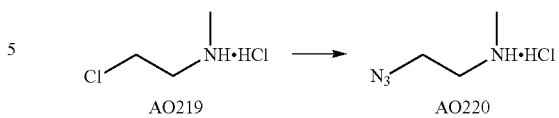

To a solution of compound AO219 (567 mg, 4.36 mmol, 1.0 equiv.) in water (20 mL) was added sodium azide (850 mg, 13.1 mmol, 3.0 equiv.). After 18 h of stirring at 80° C., a solution of sodium hydroxide (5%) (5 mL) was added. The reaction mixture was extracted with diethyl ether (×3). The organic layer was dried over magnesium sulfate, filtered, treated by HCl (gas), concentrated and dried with a vane pump during 5 h to afford compound AO220 (476 mg, 3.48 mmol) as a white solid in 80% yield which was used in the next step without further purification. $^1$H NMR (400 MHz, MeOD) δ 3.75 (t, J=5.6 Hz, 2H, $CH_2N$), 3.17 (t, J=5.6 Hz, 2H, $CH_2N_3$), 2.73 (s, 3H, $CH_3N$). $^{13}$C NMR (100 MHz, MeOD) δ 49.05 ($CH_2N$), 48.29 ($CH_2N_3$), 33.66 ($CH_3N$).

Step 3: Preparation of Compound AO222

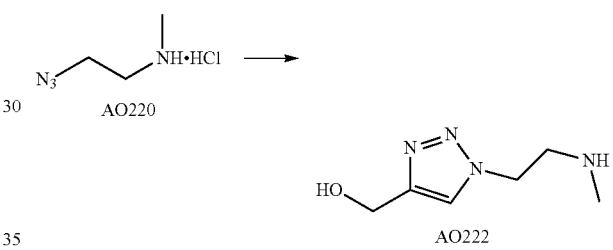

To an aqueous (40 mL) solution of $CuSO_4.5H_2O$ (864 mg, 3.46 mmol, 1.0 equiv.) were added propargylic alcohol (313 µL, 5.19 mmol, 1.5 equiv.) and sodium ascorbate (685 mg, 3.46 mmol, 1.0 equiv.). After 20 min of stirring, an aqueous (20 mL) solution of compound AO220 (473 mg, 3.46 mmol, 1.0 equiv.) was added to the reaction mixture. After 24 h of stirring at 50° C., the reaction mixture was filtered on a glass frit. The filtrate was washed with dichloromethane, and the pH was then adjusted to 10 by addition of KOH. After filtration, the aqueous solution was concentrated in vacuo and extracted several times with dichloromethane. The organic layer was dried over magnesium sulfate, filtered, concentrated and dried briefly with a vane pump to afford compound AO222 (366 mg, 2.34 mmol) as a white solid in 68% yield which was used in the next step without further purification. $^1$H NMR (400 MHz, $CDCl_3$) δ 7.63 (s, 1H, CH=C), 4.80 (s, 2H, $CH_2O$), 4.46 (t, J=5.8 Hz, 2H, $CH_2N$), 3.08 (t, J=5.8 Hz, 2H, $CH_2N$), 2.45 (s, 3H, $CH_3N$), 1.61 (se, 2H, OH, NH). $^{13}$C NMR (100 MHz, $CDCl_3$) δ 147.46 (C=C), 122.26 (CH=C), 56.73 ($CH_2O$), 51.04 ($CH_2N$), 50.01 ($CH_2N$), 36.00 ($CH_3N$).

Step 4: Preparation of Compound AO224

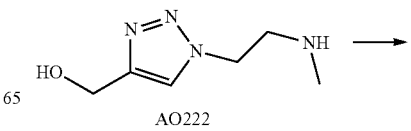

-continued

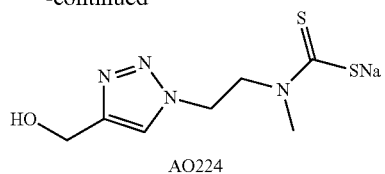

AO224

To a solution of compound AO222 (366 mg, 2.34 mmol, 1.0 equiv.) in anhydrous tetrahydrofuran (25 mL) was added, at 0° C. under argon and dropwise, carbon disulfide (212 µL, 3.51 mmol, 1.5 equiv.). After 5 min of stirring at 0° C., sodium hydride (60% dispersion in mineral oil) (94 mg, 2.34 mmol, 1.0 equiv.) was added portionwise. After 30 min of stirring at 0° C., the reaction mixture was concentrated in vacuo. The resulting crude product was dissolved in a mixture of methanol/cyclohexane (1/1). After layer separation, the methanol layer was washed by cyclohexane and concentrated in vacuo. The gummy solid was dissolved in a minimal amount of dichloromethane, diluted by diethyl ether, concentrated in a vacuo and dried with a vane pump during one night to afford compound AO224 (444 mg, 1.75 mmol) as a brown solid in 69% yield which was used in the next step without further purification. $^1$H NMR (400 MHz, MeOD) δ 7.93 (s, 1H, CH=C), 4.68 (s, 2H, CH$_2$O), 4.51 (t, J=6.2 Hz, 2H, CH$_2$N), 3.04 (t, J=6.2 Hz, 2H, CH$_2$N), 2.39 (s, 3H, CH$_3$N). $^{13}$C NMR (100 MHz, MeOD) δ 149.10 (C=C), 124.51 (CH=C), 56.48 (CH$_2$O), 51.76 (CH$_2$N), 50.50 (CH$_2$N), 35.74 (CH$_3$N).

Step 5: Preparation of Compound AO225

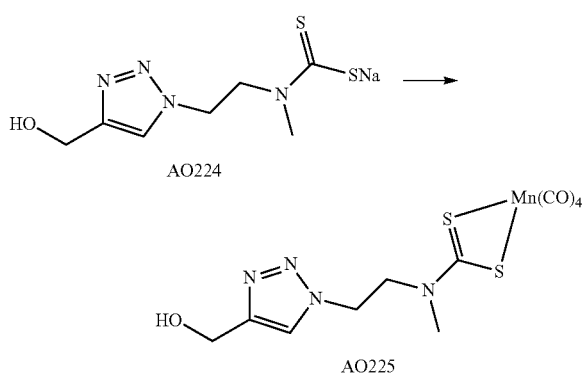

To a solution of compound AO224 (444 mg, 1.75 mmol, 1.0 equiv.) in methanol (30 mL) was added Mn(CO)$_5$Br (487 mg, 1.75 mmol, 1.0 equiv.). After 3 h of stirring at 45° C. under argon, the reaction mixture was concentrated in vacuo, dissolved in ethyl acetate, filtered on celite and concentrated in vacuo to afford compound AO225 (464 mg, 1.16 mmol) as a yellow oil in 67% yield which was used in the next step without further purification. $^1$H NMR (400 MHz, MeOD) δ 7.93 (s, 1H, CH=C), 4.75 (t, J=5.7 Hz, 2H, CH$_2$N), 4.67 (s, 2H, CH$_2$O), 4.26 (t, J=5.6 Hz, 2H, CH$_2$N), 3.19 (s, 3H, CH$_3$N). $^{13}$C NMR (100 MHz, MeOD) δ 210.99 (CO$_{metal}$), 177.03 (CS$_2$), 149.30 (C=C), 124.76 (CH=C), 56.50 (CH$_2$O), 51.63 (CH$_2$N), 47.86 (CH$_2$N), 37.31 (CH$_3$N). $^{55}$Mn NMR (100 MHz, MeOD) δ-1019.2.

Step 6: Preparation of Compound I:

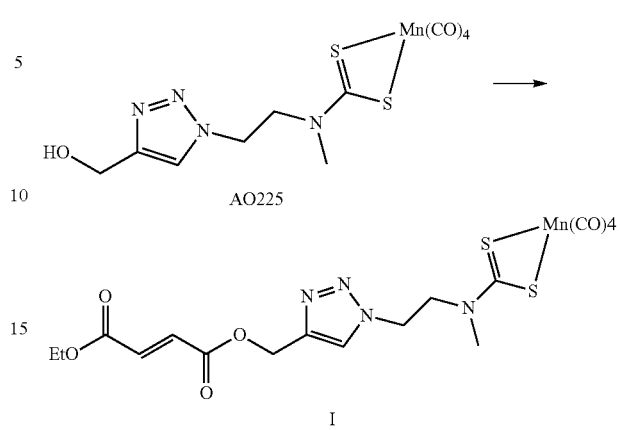

To a solution of compound AO225 (462 mg, 1.16 mmol, 1.0 equiv.) in anhydrous dichloromethane (15 mL) were added under argon (E)-4-chloro-4-oxo-2-butenoic acid ethyl ester (282 mg, 1.74 mmol, 1.5 equiv.) and 4-DMAP (213 mg, 1.74 mmol, 1.5 equiv.). After 16 h of stirring at 40° C. under argon, the reaction mixture was concentrated in vacuo. The resulting crude product was washed with cyclohexane, dried, dissolved in a minimal amount of dichloromethane and diluted with cyclohexane in order to be precipitated. After filtration and drying, the residue was extracted with ethyl acetate (×6). The organic layer was filtered on celite, concentrated in vacuo, dried with a vane pump and cristallized in a mixture of petrol ether and ethyl acetate to afford Compound as a yellow solid in 25% yield. $^1$H NMR (400 MHz, CDCl$_3$) δ 6.96 (d, J=16.0 Hz, 1H, CH=C), 6.91 (d, J=15.9 Hz, 1H, CH=C), 6.81 (s, 1H, CH=C), 5.12 (s, 2H, CH$_2$O), 3.86 (q, J=7.2 Hz, 2H, CH$_2$O), 3.53 (t, J=6.2 Hz, 2H, CH$_2$N), 3.11 (t, J=6.1 Hz, 2H, CH$_2$N), 2.14 (s, 3H, CH$_3$N), 0.85 (t, J=7.2 Hz, 3H, CH$_3$C). $^{13}$C NMR (100 MHz, CDCl$_3$) δ 205.06 (CO$_{metal}$), 164.75 (CO$_{ester}$), 164.74 (CO$_{ester}$), 143.09 (C=C), 134.65 (CH=C), 132.88 (CH=C), 124.55 (CH=C), 61.14 (CH$_2$O), 58.38 (CH$_2$O), 50.24 (CH$_2$N), 45.85 (CH$_2$N), 36.98 (CH$_3$N), 13.92 (CH$_3$C). $^{55}$Mn NMR (100 MHz, CDCl$_3$) δ-1011.8.

Example 2: Assessment of CO-Release by Compounds of the Invention

Assessment of CO-Release in Myoglobin Oxidation Assay by Compounds A and B:

Myoglobin (lyophilized horse heart; 44 µM final concentration) was prepared in 1× phosphate buffered saline (PBS, pH 7.4) in a cuvette from a 500 µM stock solution and converted to deoxymyoglobin (deoxyMb) by adding sodium dithionite. The solution was maintained at 37° C. in the spectrophotometer chamber throughout the assay using a JASCO temperature controller. A deoxyMb spectrum was recorded, revealing a characteristic peak at 560 nm. A 2-fold excess of a CO—RM molecule was then added to the cuvette to obtain a maximum carbonmonoxy-myoglobin (Mb-CO) spectrum (saturated Mb-CO). As expected for Mb-CO spectra, typical absorption peaks at 542 and 576 nm were observed. The release of CO from compound A, compound B (30 µM) or the curcumin-CO—RM according to WO 2012/076696 (30 µM) of the following formula:

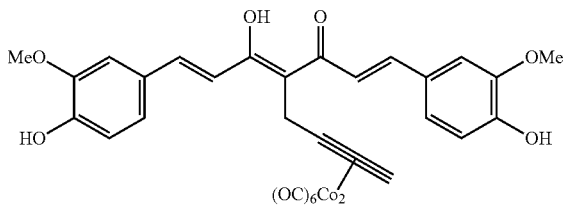

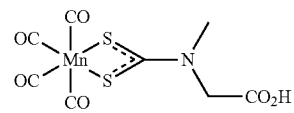

was measured by adding the compounds to 44 µM deoxyMb and the solution overlaid with 400 µl olive oil to prevent loss of CO or oxygen diffusion, which would compete with CO binding to myoglobin. Samples were scanned immediately after addition of the compounds and at consecutive time-points to monitor the formation of Mb-CO (µM).

Raw Mb-CO data were corrected using a 4-point non-linear regression method to compensate for a shift in absorbance due to the CO-releasing compounds. The concentration of Mb-CO at each time-point was calculated using the absorbance values at 540 nm and the extinction coefficient derived from the saturated Mb-CO spectrum, as described previously.[5] Mb-CO concentrations (µM) were plotted against time (min) and $t_{1/2}$ were determined using GraphPad Prism software version 5.0 (San Diego, Calif.) by applying a Boltzmann sigmoidal non-linear regression curve fit. $t_{1/2}$ represent the time taken for the concentration of Mb-CO to equal half the maximum Mb-CO formed under the assay conditions.

The presence of absorption peaks at 540 and 578 nm indicates the formation of MbCO by the carbon monoxide released by the CO—RM molecules.

The results are presented in FIG. 1A-C.

As shown by these results, compound A and compound B release carbon monoxide whereas the curcumin derivative according to WO 2012/076696 does not.

Figure 6:
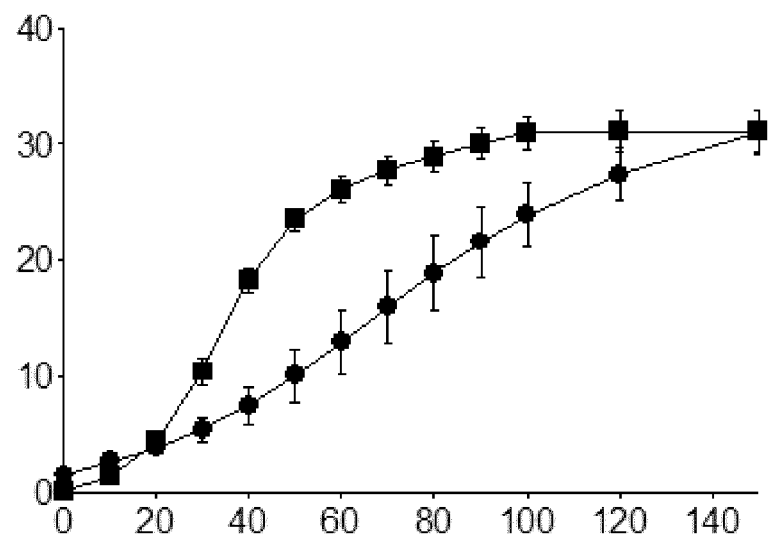
FIG. 6 represents the concentration of CO released (Y axis, expressed as the amount of carbon monoxy myoglobin detected in µM) as a function of time (X axis, expressed in minutes) using deoxymyoglobin (Mb, 100 µM) in the presence of compound A (FIG. 6A, -■-) and compound B (FIG. 6A and FIG. 6B, -●-).
Figure 6:
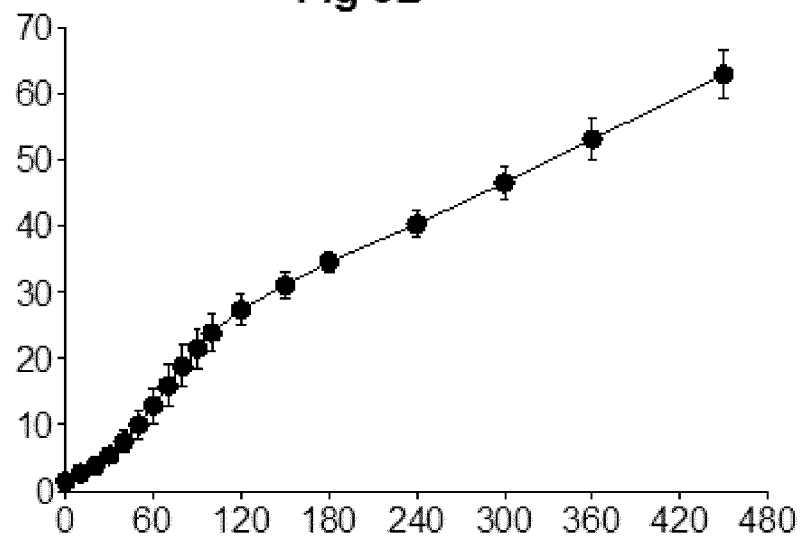

The amount of CO released was also measured as a function of time for compounds A and B. The results are presented in FIG. 6.

The results indicate that compound A liberates CO with a faster rate compared to compound B, but the amount of CO finally liberated is much higher in the case of compound B in accordance with the presence of two bi-metallic carbonyl complexes.

It can thus be concluded that the monometallic hybrids of formula (Ia) release CO at a faster rate compared to the bi-metallic hybrid of formula (Ic), but the amount of CO finally released is much higher in the case of compound (Ic), in accordance with the presence of two bi-metallic carbonyl complexes. The compounds of formula (Ia) are therefore advantageous for a fast biological activity (burst effect). However, since the bi-metallic hybrids of formula (Ic) are able to release more CO over a longer period of time, they are advantageous for a sustained biological activity.

Detection of CO in BV2 Microglia Exposed to Compound C in COP-1 Assay

In order to detect the CO release, BV2 microglia cells ($10^6$ cells/ml) were washed once, incubated with PBS containing $Ca^{2+}$ and $Mg^{2+}$ and then treated for 15 min in the dark at 37° C. with compound C and comparative compound CORM-401 according to WO 2008/003953 (5 µM) of the following formula:

Comparative compound CORM 401. Cells were then loaded with the CO sensitive fluorescent probe COP-1 (0.001 mM) for 30 min in the dark at 3TC. Results were expressed as the corrected mean fluorescence intensity (MFIc) using flow cytometry. $MFIc = MFI_{stained\ treated\ cells} - MFI_{COP\text{-}1\ background}$.

Figure 1D:
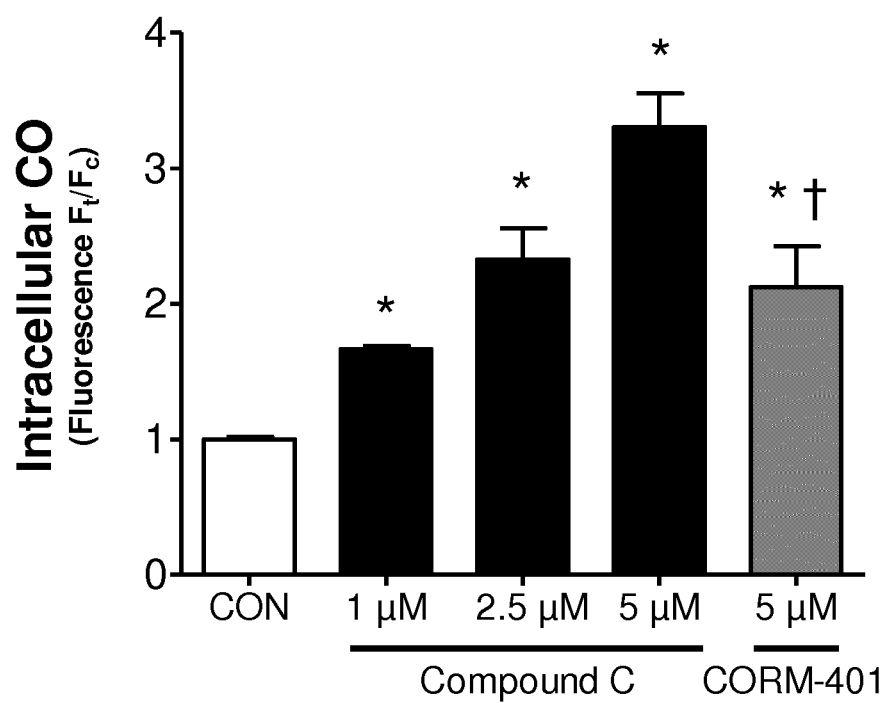

The results are presented in FIG. 1D.

As shown by these results, compound C releases significantly more carbon monoxide than the comparative compound CORM-401 according to WO 2008/003953.

These results demonstrate that the fumarate moiety of the compounds of the invention induces a positive effect on in cellulo carbon monoxide release. Moreover, these results demonstrate that the combination of a fumarate moiety with a CO-releasing molecule (CORM) has a synergistic action on carbon monoxide release.

Example 3: Assessment of the Biological Activity of Compounds A and B

Example 3.1a: Assessment of Heme Oxygenase Activity with Compounds A and B

Heme oxygenase activity was determined by a spectrophotometric assay that measures the formation of bilirubin as a difference in absorbance between 464 and 530 nm (extinction coefficient for bilirubin 40 $mM^{-1} \cdot cm^{-1}$). BV2 microglia was incubated with increasing concentrations of compound A for 6 h. Following incubation, cells were harvested in ice cold PBS (pH 7.4) containing 2 mM $MgCl_2$ and stored at −80° C. Cell samples were incubated in the dark at 37° C. for 1 h in a reaction mix containing PBS/$MgCl_2$, 20 µM hemin (Frontier Scientific, Newark, Del.) as a heme oxygenase substrate, rat liver cytosol as a source of biliverdin reductase, 2 mM glucose-6-phosphate, 0.5 U/ml glucose-6-phosphate dehydrogenase and 0.8 mM NADPH. The reaction was terminated by addition of 1 ml pure chloroform and a solution containing only bilirubin was extracted by vortex-centrifugation cycles. Absorbance values corresponding to the formation of bilirubin were obtained using an Ultraspec™ 500 pro visible spectrophotometer (GE Healthcare Life Sciences) and the data presented as pmoles bilirubin/mg protein/h. Protein concentrations were measured using a Pierce BCA Protein Assay kit (Thermo Scientific).

The results are presented in FIG. 2A.

The results show that compound A improves significantly HO-1 activity at a concentration as low as 5 µM.

Example 3.1b: Assessment of Heme Oxygenase Activity with Compound C

Heme oxygenase activity of compound C was determined as described above and was compared to comparative compound CORM-401 and to comparative fumarate derivative (compound J:

Compound J

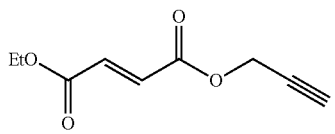

The results are presented in FIG. 2B.

These results show that compound C significantly improves HO-1 activity at a concentration as low as 1 μM. Furthermore, compound C exhibits an improved HO-1 activity compared to comparative compound J, which is a fumarate derivative not comprising any CORM. This thus demonstrates that the combination of a fumarate moiety and a CO-releasing molecule (CORM) has a synergistic action on Heme oxygenase activity.

Example 3.2: Effect of Compound a, Compound B and Compound C on Inflammation

Determination of Nitrite Production

Nitrite production, an index of inflammation, was measured in BV2 cells challenged for 24 h with lipopolysaccharide (LPS, 1 μg/ml) in the presence or absence of increasing concentrations of compound A or compound B. At the end of the incubation, nitrite levels were measured using the Griess method.[12,14] Briefly, cell plates were centrifuged at 10,000×g for 5 min and the cell-free supernatant was incubated with an equal volume of Griess reagent (2 mM N-(1-naphtyl)ethylenediamide, 30 mM sulfanilamide and 140 mM o-phosphoric acid) for 10 min at room temperature. The absorbance was measured at 560 nm. Concentrations of nitrite (μM) were calculated from a standard curve of sodium nitrite.

Figure 3:
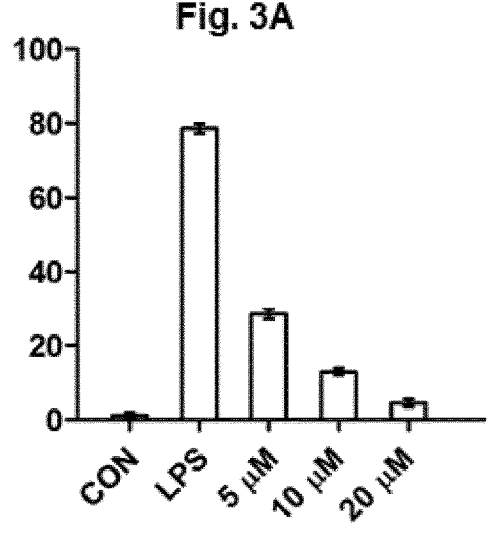
FIG. 3 represents on the Y axis nitrite production expressed in µM in BV2 microglia (CON), in BV2 microglia challenged for 24 h with lipopolysaccharide (LPS, 1 µg/ml) (LPS) and in BV2 microglia challenged with lipopolysaccharide (LPS, 1 µg/ml) (LPS) in the presence of increasing concentrations of compound A (FIG. 3A) or compound B (FIG. 3B).
Figure 3:
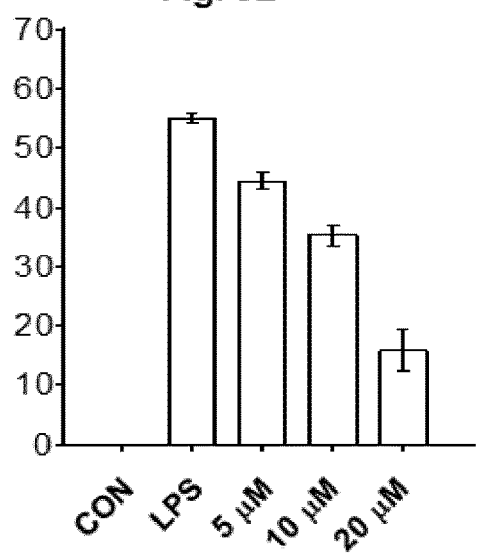
Figure 3:
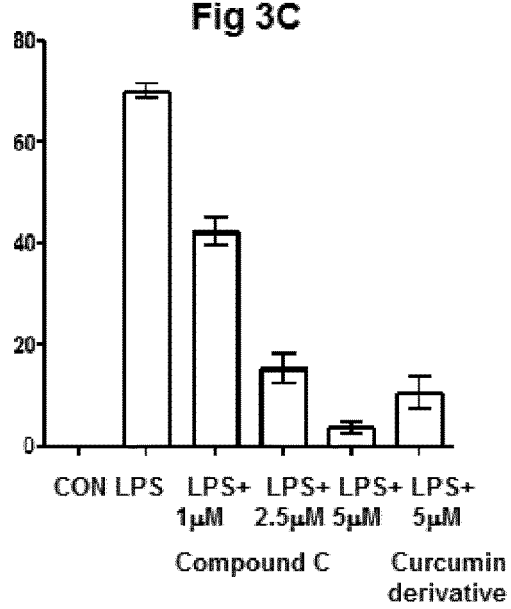

The results are presented in FIG. 3.

Compound A markedly decreased LPS-mediated nitrite accumulation, showing that the $Co_2(CO)_6$ group contributes to the reduction of nitrite levels. Surprisingly, compound B also decreased nitrite production in a concentration-dependent manner but was not as effective as compound A.

Compound C was also assessed for its capacity to reduce nitrite level in a comparative assay with a curcumin derivative according to WO 2012/076696 of the following formula:

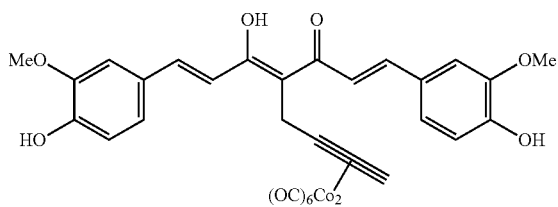

The results are presented in FIG. 3C.

As evidenced by these results, compound C is significantly more active (by an almost 2-fold) than the curcumin derivative according to WO 2012/076696, since the same reduction of nitrite production is observed with 2.5 μM of compound C and 5 μM of the curcumin derivative.

Compound C was also assessed for its capacity to reduce nitrite level in a comparative assay with comparative compounds CORM-401 and comparative compound J described above.

Figure 3D:
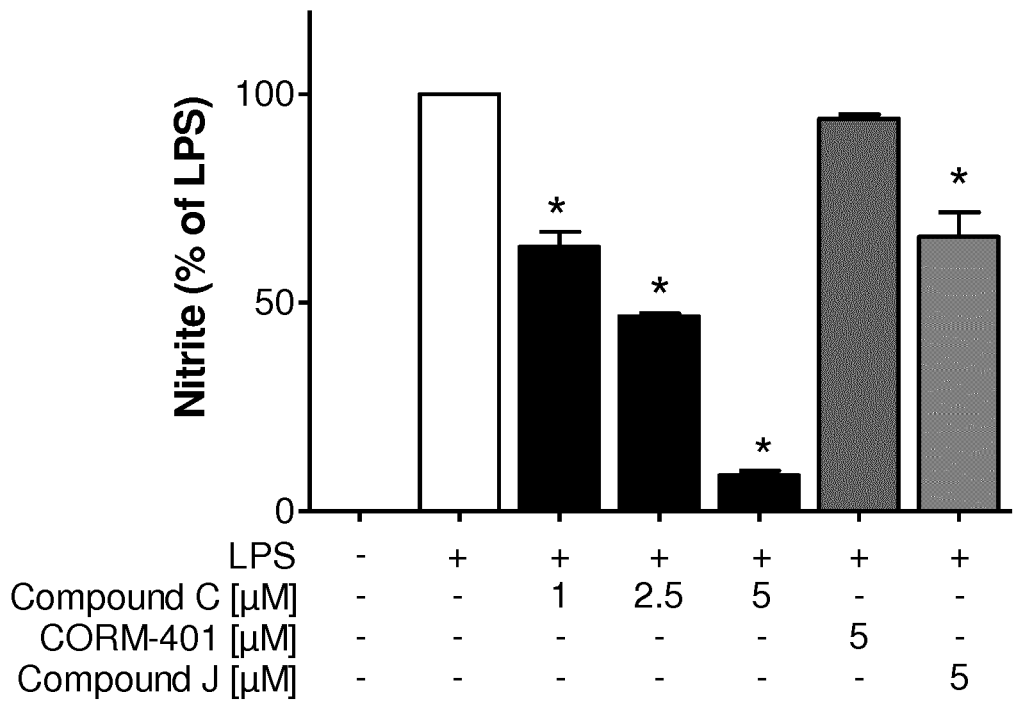
FIG. 3C and FIG. 3D represent on the Y axis nitrite production expressed in µM in BV2 microglia (CON), in BV2 microglia challenged for 24 h with lipopolysaccharide (LPS, 1 µg/ml) and in BV2 microglia challenged with lipopolysaccharide (LPS, 1 µg/ml) (LPS) in the presence of increasing concentrations of compound C (1, 2.5 and 5 µM) and in the presence of 5 µM of a curcumin derivative according to WO 2012/076696 (FIG. 3C) or in the presence of 5 µM of comparative fumarate derivative (compound J) and comparative compound CORM-401 of WO 2008/003953 (FIG. 3D).

The results are presented in FIG. 3D.

TABLE 1

Comparison of the anti-inflammatory potency of comparative compound dimethylfumarate, comparative compound J and compound A.

| Compound (5 μM) | Nitrite levels (μM) | | % decrease vs. |
|---|---|---|---|
| | LPS | LPS + compound | LPS |
| Dimethylfumarate | 86.3 ± 2.9 | 69.2 ± 1.0* | 19.8% |
| Compound J | 86.7 ± 1.6 | 43.2 ± 1.0*† | 50.1% |
| Compound A | 78.0 ± 1.3 | 28.6 ± 1.3*†‡ | 63.3% |

Nitrite levels were measured in cell following 24 hr incubation with 0.5 μg/ml lipopolysaccharide (LPS) ±5 μM of comparative compound dimethylfumarate comparative compund J or Compound A.
All values (mean ± SEM) are shown as percentage of LPS alone.
*p < 0.05 vs. LPS alone; †p < 0.05 vs. dimethylfumarate; ‡p < 0.05 vs. comparative compounds.

As evidenced by these results, compound C is significantly more active (by almost 5-fold) than the fumarate derivative (comparative compound J), since almost the same reduction of nitrite production is observed with 1 μM of compound C and 5 μM of the fumarate derivative J. Furthermore, comparative compound CORM-401 is not active.

Compound A was also compared to dimethylfumarate derivative (comparative compound J) in the nitrite production assay. As shown by table 1, compound A allows a significant decrease of the inflammation caused by LPS (63.3%), which is more than 3 fold the decrease induced by the same concentration of dimethylfumarate derivative (comparative compound J). These results thus demonstrate that the combination of a fumarate moiety with a CORM induces a great benefit in disease treatment, more particularly inflammation treatment.

A CORM derivative according to WO 2008/003953 of the following formula:

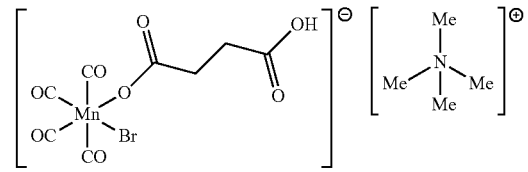

(compound 364 of WO 2008/003953) was evaluated in a comparative nitrite production assay.

Figure 3E:
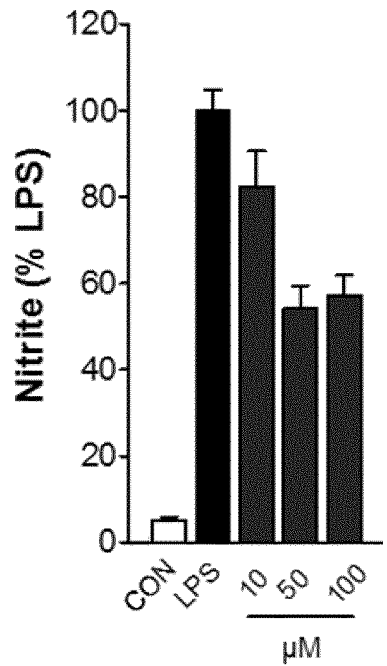

As shown in FIG. 3E, compound 364 of WO 2008/003953 was able to decrease the nitrite production for less than 50% at a concentration as high as 100 μM. Compound 364 of WO 2008/003953 is thus for a lot less active than compound A of the present invention, which decreases nitrite production by more than 60% at a concentration as low as 5 μM (Table 1).

Example 3.3: Assessment of the Cytotoxicity of Compounds of the Invention

Assessment of the Cytotoxicity of Compound A and Compound B on RAW Macrophages

Cytotoxicity was evaluated in BV2 microglia cells 24 h after incubation with increasing concentrations of compound A or compound B and on RAW macrophages with a curcumin derivative according to WO 2012/076696 of the following formula:

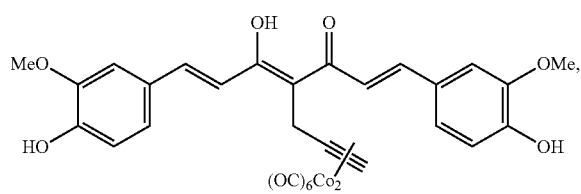

using a Cytotoxicity Detection Kit (LDH) (Roche Applied Science) to measure lactate dehydrogenase released from damaged cells. X-100 Triton solution (2%) prepared in medium was used as a positive control (100% cytotoxicity). The assay was performed according to the manufacturer's instructions. Briefly, at the end of the incubation, cell plates were centrifuged at 300×g for 5 min and 100 µl cell-free supernatant transferred to a 96-well plate. A reaction mixture was added to the supernatant and the plate was incubated in the dark at room temperature with gentle shaking for 10 min. Absorbance was measured at 485 nm.

Data are expressed as percentage of LDH released by treating cells with 2% triton (100% toxicity).

Figure 4:
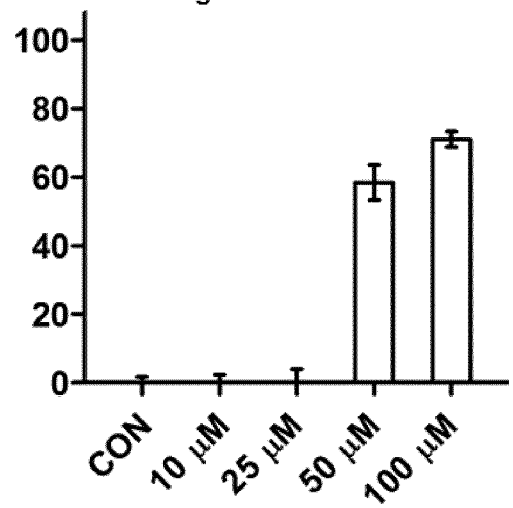
FIG. 4 represents the cytotoxicity of compound A (FIG. 4A), compound B (FIG. 4B) measured in BV2 microglia and a comparative curcumin derivative according to WO 2012/076696 (FIG. 4C) measured in RAW macrophage, compound A measured in keratinocyte cells (FIG. 4D), or compound A measured in THP-1 cells (FIG. 4E) as percentage of control (Y axis) with increasing concentration of compound A or B (X axis).
Figure 4:
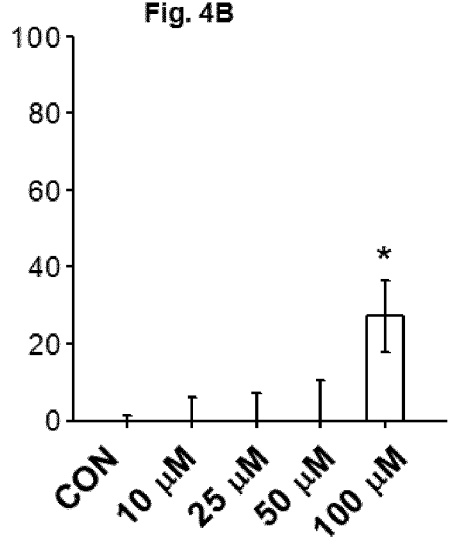
Figure 4:
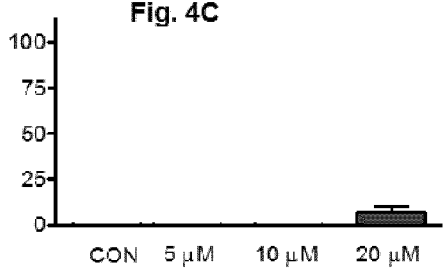
Figure 4D:
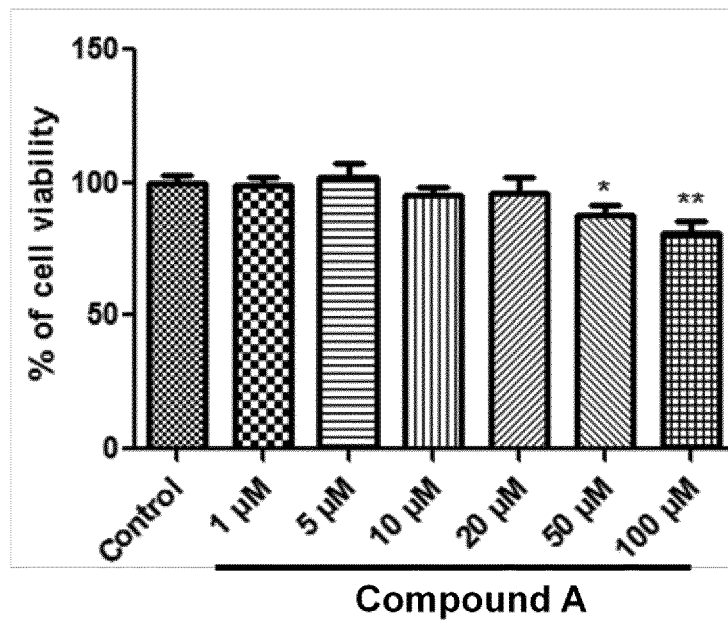

The results are presented in FIG. 4.

Cytotoxicity of compound A is not significant at concentrations below 50 µM.

Compound B only exhibits cytotoxicity at a concentration of 100 µM and is not cytotoxic below this concentration.

In contrast, the curcumin derivative according to WO 2012/076696 already exhibits cytotoxicity at a concentration of 20 µM on RAW macrophages Assessment of the Cytotoxicity of Compound A on Keratynocyte Cells Cytotoxicity was evaluated in keratynocyte cells 24 h after incubation with increasing concentrations of compound A.

Human keratinocytes (HaCaT cells) were cultured in Dulbecco's Modified Eagle Medium (DMEM) supplemented with 1% penicillin/streptomycin, 1% sodium pyruvate and 10% fetal bovine serum. Cells at confluence were washed with PBS and treated with compound A at different concentrations and for different periods of time according to the experimental protocol. Compound A was dissolved in DMSO at 0.1% as a final concentration in complete medium.

When cells in 24 well plates were confluent, culture medium was replaced with fresh medium prior to treatment with Compound A at different concentrations (1-100 µM) for 24 h. Cells were incubated overnight at 37° C. in a humidified 5% $CO_2$. DMSO 100% was used as a positive control. 24 h later cells were incubated with a MTT solution (0.5 mg/ml) for 1 h 30 min. Treatment of living cells with MTT produced a dark blue formazan product, whereas no staining is observed in dead cells.

Figure 4E:
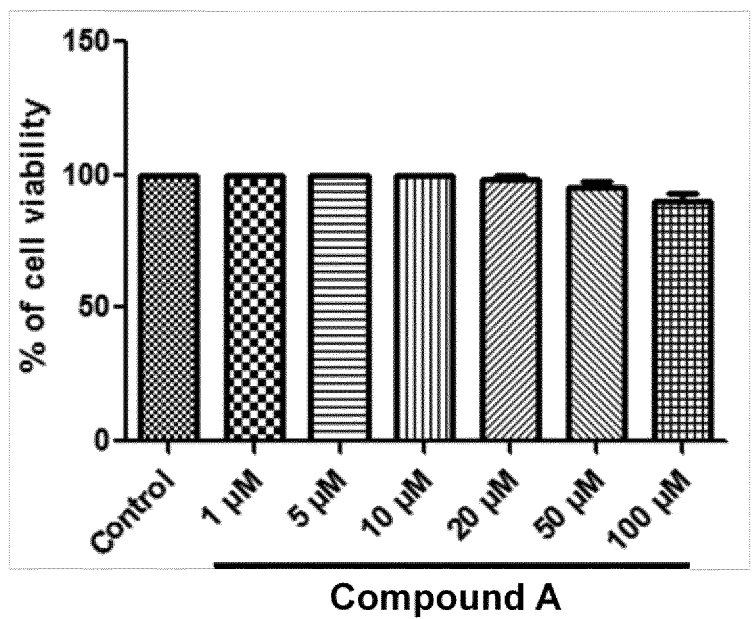

The results are presented in FIG. 4E.

Cytotoxicity of compound A is not significant at concentrations below 50 µM.

Assessment of the cytotoxicity of compound A on THP-1 cells

Cytotoxicity was evaluated in THP-1 cells 24 h after incubation with increasing concentrations of compound A.

Human monocytes (THP-1 cells) were cultured in RPMI 1640-Glutamax medium supplemented with 1% penicillin/streptomycin, 1% sodium pyruvate and 10% fetal bovine serum (RPMIc). Cells at confluence were washed with PBS and treated with compound A at different concentrations and for different periods of time according to the experimental protocol. Compound A was dissolved in DMSO at 0.1% as a final concentration in complete medium.

Before the treatment, cells were washed once with RPMI, counted and then seeded at 1×10⁶ cells/mi. Cells were then treated for 24 h with Compound A at different concentrations (1-100 µM). 24 h later, the supernatants of the different conditions were collected and the LDH assay was assessed using the cytotoxity detection kit (LDH) (Roche, Germany) according to the manufacturer's instructions. Triton 2% was used as a positive control.

The results are presented in FIG. 4E.

Cytotoxicity of compound A is not significant at concentrations below 100 µM.

Example 3.4: Assessment of Nrf-2 Expression

Assessment of Nrf-2 Expression Induced by Compound A, Compound B, Compound C and of HO-1 Expression by Compound A and Compound C.

BV2 microglia was incubated with 20 µM of compound A or compound B for 2 h to assess nuclear translocation of Nrf2. Nuclear fractions were isolated using a Nuclear Extract Kit from Active Motif (La Hulpe, Belgium), according to the manufacturer's instructions, and stored at −80° C. Protein concentrations were measured using a Pierce BCA Protein Assay kit (Thermo Scientific).

To determine HO-1 protein expression, BV2 microglia was incubated with increasing concentrations of compound A for 6 h. At the end of the incubation cells were washed with ice cold DPBS (—Ca, —Mg; Gibcow Cell Culture, Life Technologies) and lysed during 30 min incubation at 4° C. in cell lysis buffer (50 mM HEPES, 150 mM NaCl, 50 mM NaF, 50 µM $Na_3VO_4$, 1% v/v Triton X-100 and 1% mammalian protease inhibitor). Lysates were centrifuged for 10 min at 15,000×g and 4° C.; supernatants were collected and stored at −80° C. Protein concentrations were measured using a Pierce BCA Protein Assay kit (Thermo Scientific).

Nuclear extracts (50 µg protein/sample) and whole cell lysates (20 µg protein/sample) were resolved on 10 or 12% acrylamide gels, respectively, and proteins transferred to polyvinylidene difluroride membranes (Millipore, Brussels, Belgium). Membranes were blocked for 1 h at room temperature in 1× Tris-buffered saline (pH 7.5) containing 0.1% v/v TWEEN 20 and 5% w/v non-fat dry milk and incubated overnight at 4° C. with the following primary antibody for Nrf2: clone C-20 rabbit polyclonal, Santa Cruz Biotechnology). Membranes were then incubated with secondary antibodies coupled to horseradish peroxidase (goat anti-mouse or anti-rabbit, Cell Signaling Technology or donkey anti-goat, Jackson ImmunoResearch) for 1 h at room temperature. Bands were detected with chemiluminescent substrates (Pierce ECL®, Thermo Scientific or RevelBIOt® Intense, Ozyme) and images captured using a G:Box F3 Imagery Station and GeneSys Software (Syngene, Cambridge, UK).

The results are presented in FIG. 5A-C.

Exposure of BV2 microglia cells to 20 µM of compound A for 2 h strongly promoted the accumulation of Nrf2 in the nucleus. In addition, after 6 h of treatment, compound A induced a concentration-dependent increase in HO-1 protein expression. Compound B was less effective both as an Nrf2 activator and HO-1 inducing agent.

These experiments demonstrate that compound A, compound B and compound C are potent activators of HO-1 and inducers of HO-1 protein expression via the Nrf2/HO-1 axis at concentrations well below the toxic concentration range.

Moreover, comparison of compound C activity with comparative compounds CORM-401 and J shows that, at identical concentrations (5 μm), compound C is more potent than fumarate derivative (comparative compound J) and comparative compound CORM-401 at Nrf2 and HO-1 activation (FIG. 5C).

Induction of Nrf2 and HO-1 by Compound C in Keratinocyte Cells

Figure 5D:
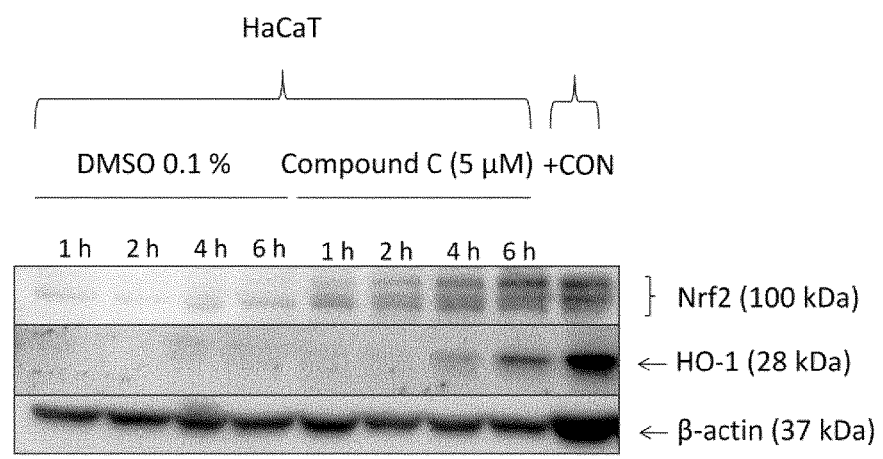
FIG. 5D represents HO-1 expression and Nrf-2 expression in keratinocyte cells over time in the presence of compound C.

Exposure of keratynocyte cells to 5 μM of compound C over time strongly promoted the accumulation of Nrf2 in the nucleus and the HO-1 protein expression (FIG. 5D).

These experiments demonstrate that compound C is, in keratinocyte cells, a potent activator of HO-1 via the Nrf2/HO-1 axis at concentrations well below the toxic concentration range. Hence, it can be used for the treatment of inflammatory diseases, more particularly skin inflammation such as wound healing or psoriasis.

Induction of Nrf2 and HO-1 by Compound C in THP-1

Figure 5E:
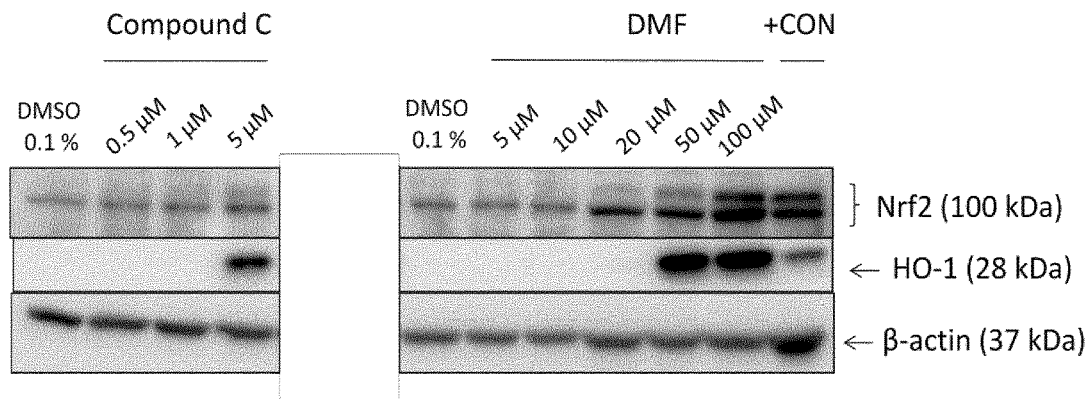
FIG. 5E represents HO-1 expression and Nrf-2 expression in keratinocytes cells in the presence of increasing concentration of compound C or comparative dimethylfumarate (DMF) or comparative positive control C+ (cynnamaldehyde, 100 µM) which are known to activate Nrf2.

As for keratinocyte cells and BV2 microglia cells, exposure of THP-1 cells to compound C for 6 hours strongly promoted the accumulation of Nrf2 in the nucleus and the HO-1 protein expression (FIG. 5E). Furthermore, when compared with HO-1 activation with comparative compound J, compound C induced a concentration-dependent increase in HO-1 protein expression starting from 5 μM of compound C, whereas 10 fold this concentration is needed to observe the same results with comparative compound J.

These experiments demonstrate that compound C is a potent activator of HO-1 via the Nrf2/HO-1 axis also in THP-1 cells.

Hence, it has been demonstrated that the compounds of the invention can be used for the treatment of inflammatory diseases.

Induction of Nrf2 and HO-1 by Compounds A, B and C in THP-1

Figure 5F:
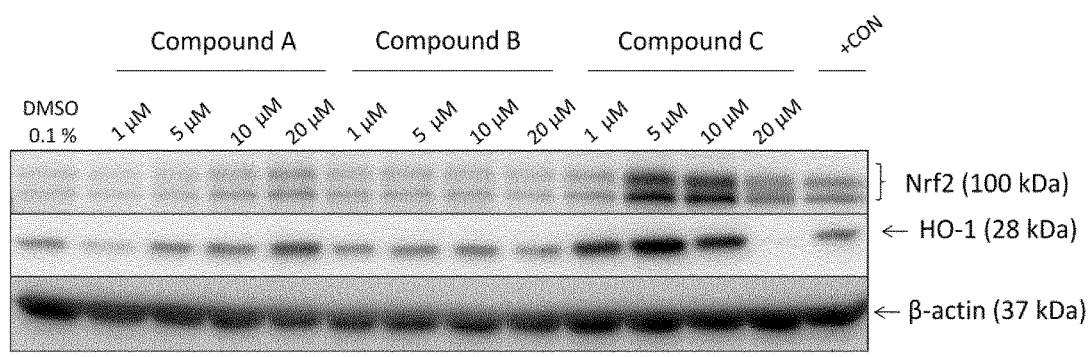
FIG. 5F represents HO-1 expression and Nrf-2 expression in THP-1 cells in the presence of increasing concentration of compound A, compound B or compound C.

THP-1 cells were exposed to different concentration of compounds A, B, and C during 6 hours. As shown above with BV2 microglial cells, compounds A and C induced a concentration-dependent increase in HO-1 protein expression and an Nrf2 activation, whereas compound B was less effective both as an Nrf-2 activator and HO-1 inducing agent (FIG. 5F).

These experiments demonstrate that the compounds of the invention comprising only one CORM group (also referred to as mono-CORM, i.e. compounds of formula (I) wherein $R_1$ represents -Q'-Y) such as compound A and compound C, are potent activators of Nrf2 and inducers of HO-1 protein expression.

Example 4: Assessment of Compound of the Invention on TNF-α Production in Human Macrophages Challenged with LPS Human THP-1 cells (ATCC; #TIB-202) were maintained at 37° C. and 5% CO2 in RPMI 1640 GlutaMax (Gibco, France) supplemented with 10% fetal bovine serum, 1% sodium pyruvate, 1% penicillin-streptomycin and 50 μM β-mercaptoethanol. Cells were seeded in 24-well plates (5×105/well/ml) and treated with phorbol myristate acetate [PMA (50 ng/ml)] for 24 h to induce macrophage differentiation. Human macrophages were then washed with PBS, incubated with medium and treated with LPS alone or with LPS in the presence of the various compounds for 24 h. Culture media was collected after 24 h and stored at −20° C. ELISA assay for TNF-α was performed according to the manufacturer's instructions (BD OptEIA Set). Briefly, the plates (F96 maxisorp-Nunc-immuno, Thermofischer) were coated with the capture antibody overnight. Then, the plates were washed with PBS/tween 0.05% and saturated for 1 h with PBS/FBS 10% at 3TC. After several washings, standards and samples were incubated for 2 h at room temperature. Later on, detection antibody and streptavidine-HRP were incubated for 1 h at room temperature. At the end, the substrate (TMB) was added leading to a blue color. The reaction was stopped with sulfuric acid leading to a yellow color. The plates were read at 450 nm using a microplate reader. Results were expressed in picograms per ml.

Figure 7:
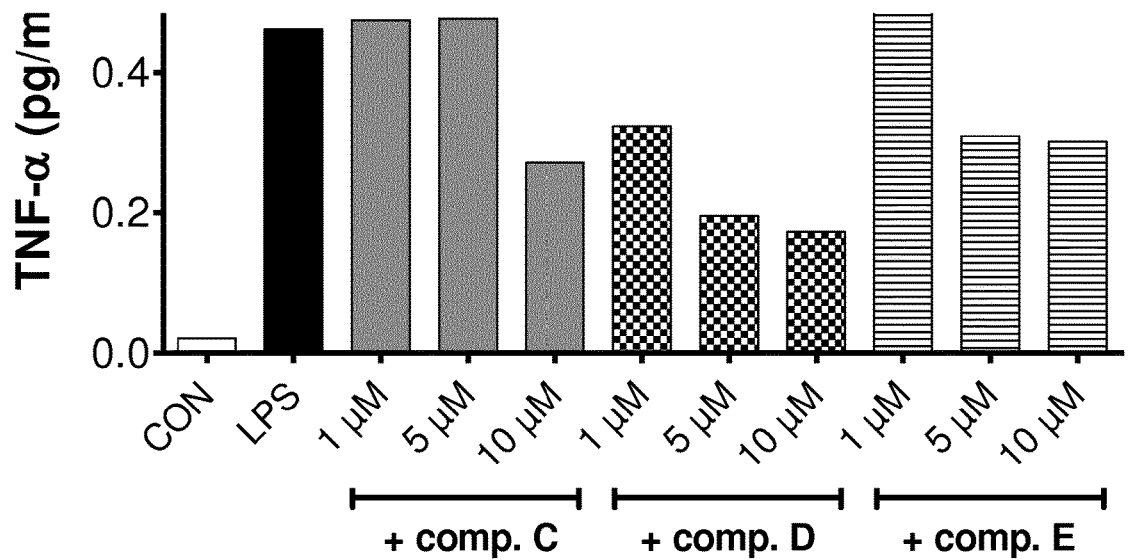
FIG. 7 represents TNF-α production in human macrophages challenged with LPS in the presence of compound C and compound E.

As shown in FIG. 7, exposure of human macrophages to LPS for 24 h resulted in a significant increase in TNF-alpha production, a marker of inflammation. This effect was significantly decreased when macrophages were co-treated with increasing concentrations (1-10 μM) of compound C, D or E. Compound D appeared to be the most effective of the three compounds tested.

Figure 8:
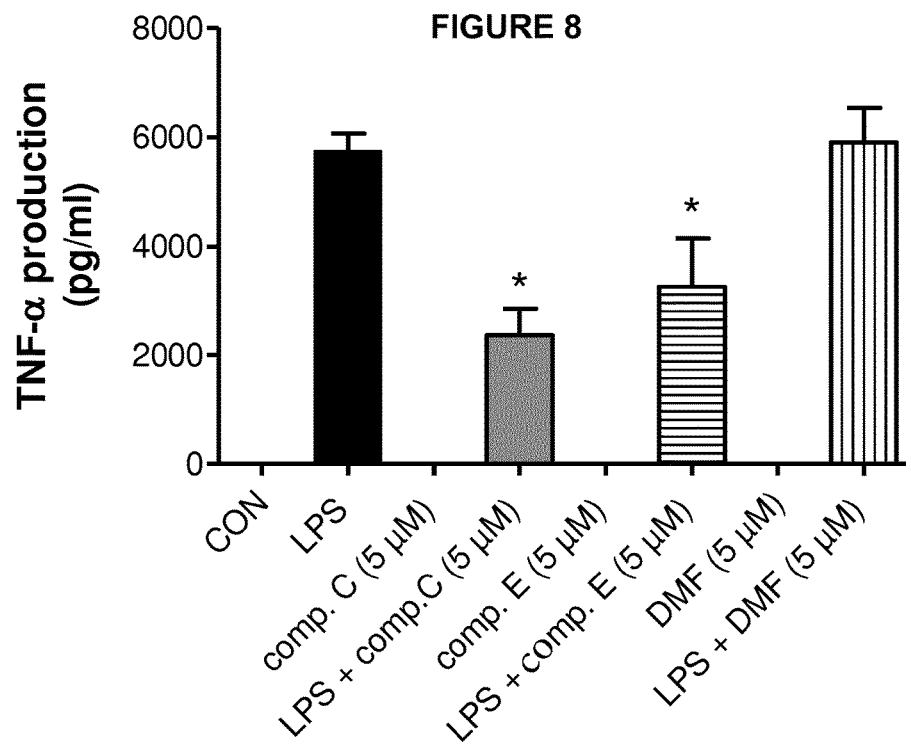
FIG. 8 represents TNF-α production in human THP-1 cells challenged with LPS in the presence of compound C and compound E.

Example 5: Assessment of Compound of the Invention on TNF-α Production in THP-1 Cells Challenged with LPS Human THP-1 cells cultured as in Example 3.3 were treated with LPS (100 μg/ml) alone or in the presence of 5 μM compound C, compound E or the comparative dimethyl fumarate (DMF) for 24 h. As shown in FIG. 8, both compound C and compound E significantly reduced TNF-α production whereas dimethyl fumarate (DMF) did not have any effect.

The invention claimed is:

1. A hybrid fumarate-carbon monoxide releasing molecule of formula (I)

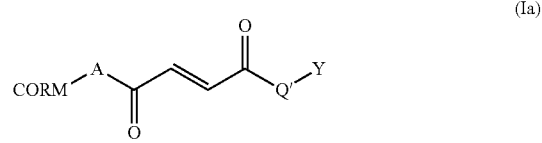

(Ia)

wherein:

A represents:

a single bond, or

—Z-Q-, where:

Q represents O, S or $NR_2$, where $R_2$ represents H, $(C_1\text{-}C_6)$alkyl, aryl, heteroaryl, $(C_1\text{-}C_6)$alkyl-aryl, $(C_1\text{-}C_6)$alkyl-heteroaryl, $(C_1\text{-}C_6)$alkyl-$(C_3\text{-}C_8)$heterocyclyl, or —$(C_3\text{-}C_{14})$cycloalkyl, or $R_2$ and Z are connected to form a $(C_3\text{-}C_8)$heterocyclyl, Z represents —$(C_1\text{-}C_6)$alkyl-, —$(C_2\text{-}C_6)$alkenyl-, -aryl-, -heteroaryl-, —$(C_2\text{-}C_6)$alkynyl-, —$(C_3\text{-}C_8)$heterocyclyl-, —$(C_3\text{-}C_{14})$cycloalkyl, —$(C_1\text{-}C_6)$alkyl-$R_3$—$(C_1\text{-}C_6)$alkyl-, —$(C_2\text{-}C_6)$alkenyl-$R_3$—$(C_1\text{-}C_6)$alkyl-, —$(C_1\text{-}C_6)$alkyl-$R_3$—$(C_2\text{-}C_6)$alkenyl-, —$(C_2\text{-}C_6)$alkenyl-$R_3$—$(C_2\text{-}C_6)$alkenyl-, —$(C_1\text{-}C_6)$alkyl-$R_3$—$(C_2\text{-}C_6)$alkynyl-, —$(C_2\text{-}C_6)$alkenyl-$R_3$—$(C_2\text{-}C_6)$alkynyl-, —$(C_2\text{-}C_6)$alkynyl-$R_3$—$(C_2\text{-}C_6)$alkynyl-, —$(C_2\text{-}C_6)$alkynyl-$R_3$—$(C_1\text{-}C_6)$alkyl-, or —$(C_2\text{-}C_6)$alkynyl-$R_3$—$(C_2\text{-}C_6)$alkenyl-, where $R_3$ represents aryl, heteroaryl, $(C_3\text{-}C_8)$heterocyclyl, $(C_3\text{-}C_{14})$cycloalkyl, —$(C_1\text{-}C_6)$alkyl-OCO—, or —$CH_2$—$(CHOR_3)CH_2O$—$(C_1\text{-}C_6)$alkyl-, CORM represents a carbonyl metal complex selected from the group consisting of:

Mn(CO)$_5$,

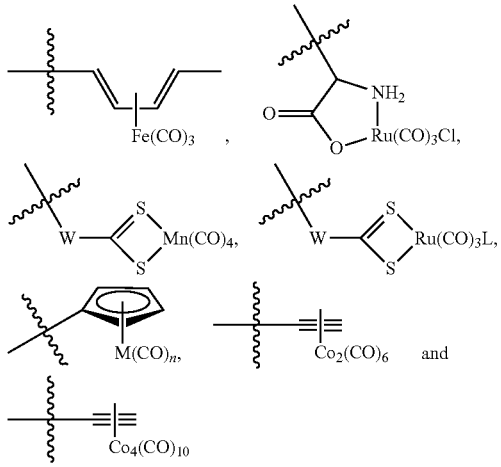

where W represents O or NR$_4$, where R$_4$ represents —(C$_1$-C$_6$)alkyl-, L represents an ionic ligand, or a counter-ion, M represents Rh, Co, Ru, Mn, Mo, V or Fe, and n is an integer chosen so that the metal M has no free valency, Q' represents O, S or NR$_5$, where R$_5$ represents H, (C$_1$-C$_6$)alkyl, aryl, heteroaryl, (C$_1$-C$_6$)alkyl-aryl, (C$_1$-C$_6$)alkyl-heteroaryl, (C$_1$-C$_6$)alkyl-(C$_3$-C$_8$)heterocyclyl, or —(C$_3$-C$_{14}$)cycloalkyl, and Y represents H, —(C$_1$-C$_6$)alkyl, —(C$_2$-C$_6$)alkenyl, -aryl, -heteroaryl, —(C$_2$-C$_6$)alkynyl, —(C$_3$-C$_8$)heterocyclyl, —(C$_3$-C$_{14}$)cycloalkyl, —(C$_1$-C$_6$)alkyl-R$_6$—(C$_1$-C$_6$)alkyl, —(C$_2$-C$_6$)alkenyl-R$_6$—(C$_1$-C$_6$)alkyl, —(C$_1$-C$_6$)alkyl-R$_6$—(C$_2$-C$_6$)alkenyl, —(C$_2$-C$_6$)alkenyl-R$_6$—(C$_2$-C$_6$)alkenyl, —(C$_1$-C$_6$)alkyl-R$_6$—(C$_2$-C$_6$)alkynyl, —(C$_2$-C$_6$)alkenyl-R$_7$—(C$_2$-C$_6$)alkynyl, —(C$_2$-C$_6$)alkynyl-R$_6$—(C$_2$-C$_6$)alkynyl, —(C$_2$-C$_6$)alkynyl-R$_6$—(C$_1$-C$_6$)alkyl, —(C$_2$-C$_6$)alkynyl-R$_6$—(C$_2$-C$_6$)alkenyl, (C$_1$-C$_6$)alkyl-R$_6$, —(C$_2$-C$_6$)alkenyl-R$_6$, —(C$_2$-C$_6$)alkynyl-R$_6$, or —CH, where R$_6$ represents aryl, heteroaryl, (C$_3$-C$_8$)heterocyclyl, or (C$_3$-C$_{14}$)cycloalkyl, and where R$_7$ represents H, (C$_1$-C$_6$)alkyl, aryl, heteroaryl, (C$_1$-C$_6$)alkyl-aryl, (C$_1$-C$_6$)alkyl-heteroaryl, (C$_1$-C$_6$)alkyl-(C$_3$-C$_8$)heterocyclyl, or (C$_1$-C$_6$)alkyl-(C$_3$-C$_4$)cycloalkyl.

2. The molecule of claim 1, wherein Q represents O, S or NR$_2$, where R$_2$ represents H, or (C$_1$-C$_6$)alkyl, and Z represents —(C$_1$-C$_6$)alkyl-, —(C$_2$-C$_6$)alkenyl-, —(C$_3$-C$_8$)heterocyclyl-, —(C$_1$-C$_6$)alkyl-R$_3$—(C$_1$-C$_6$)alkyl-, or —(C$_2$-C$_6$)alkenyl-R$_3$—(C$_1$-C$_6$)alkyl-, where R$_3$ represents heteroaryl or (C$_3$-C$_8$)heterocyclyl.

3. The molecule of claim 2 wherein Z— represents —CH$_2$—CH$_2$—,

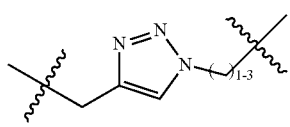

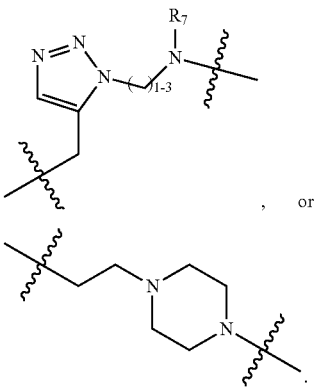

, or

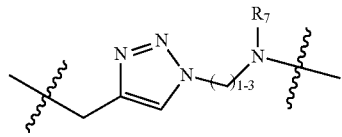

.

4. The molecule of claim 1, wherein CORM is selected from the group consisting of:

Mn(CO)$_5$,

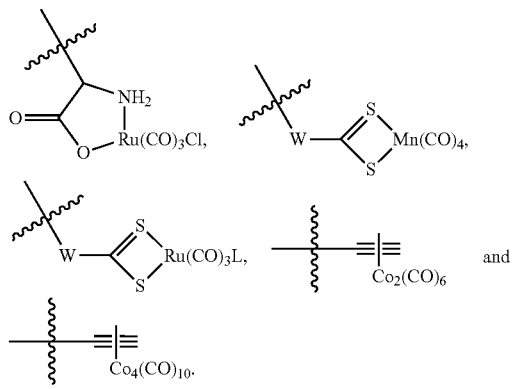

5. The molecule of claim 1, wherein Y represents H, —(C$_1$-C$_6$)alkyl, —(C$_2$-C$_6$)alkenyl, -aryl, -heteroaryl, —(C$_2$-C$_6$)alkynyl, —(C$_3$-C$_8$)heterocyclyl, —(C$_3$-C$_8$)cycloalkyl or —(C$_1$-C$_6$)alkyl-aryl.

6. The molecule of claim 1, wherein Q' is O.

7. The molecule of claim 1, wherein it is of formula (Ia1):

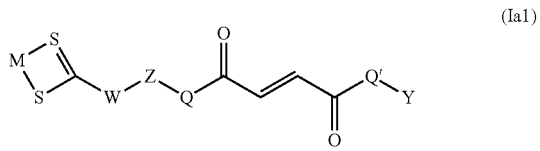

(Ia1)

with M representing Mn(CO)$_4$ or Ru(CO)$_3$Cl.

8. The molecule of claim 7, wherein Z—W represents: —CH$_2$—CH$_2$—NR$_7$—,

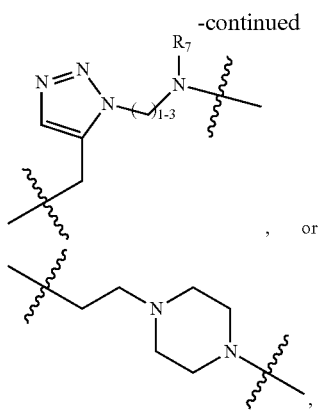

where $R_7$ represents $(C_1-C_3)$alkyl, $Q'$ represents O and Y represents H, —$(C_1-C_6)$alkyl or —$(C_2-C_6)$alkenyl.

9. The molecule of claim 1, where it is selected from the group consisting of:

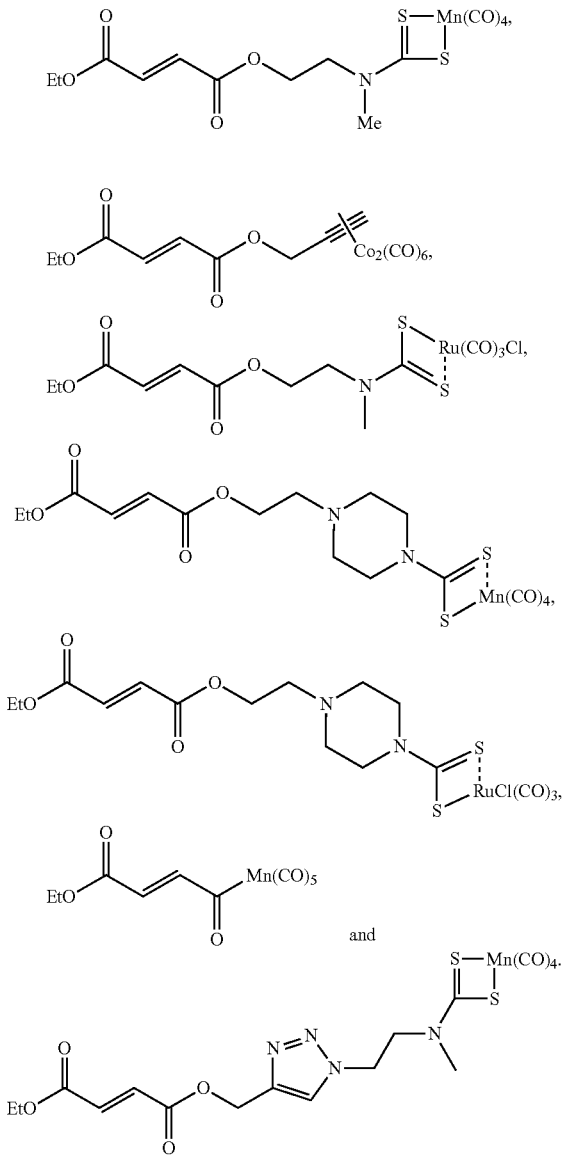

and

10. A method of treating cardiovascular or inflammatory disease comprising administering to a patient in need thereof a therapeutically effective amount of a hybrid fumarate-carbon monoxide releasing molecule of formula (I)

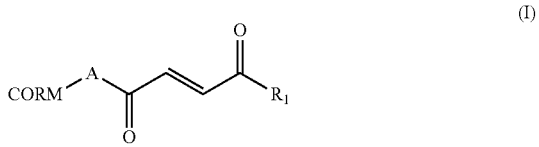

wherein:

A represents:

a single bond, or

—Z-Q-, where:

Q represents O, S or $NR_2$, where $R_2$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_8)$heterocyclyl, or —$(C_3-C_{14})$cycloalkyl, or $R_2$ and Z are connected to form a $(C_3-C_8)$heterocyclyl, Z represents —$(C_1-C_6)$alkyl-, —$(C_2-C_6)$alkenyl-, -aryl-, -heteroaryl-, —$(C_2-C_6)$alkynyl-, —$(C_3-C_8)$heterocyclyl-, —$(C_3-C_{14})$cycloalkyl, —$(C_1-C_6)$alkyl-$R_3$—$(C_1-C_6)$alkyl-, —$(C_2-C_6)$alkenyl-$R_3$—$(C_1-C_6)$alkyl-, —$(C_1-C_6)$alkyl-$R_3$—$(C_2-C_6)$alkenyl-, —$(C_2-C_6)$alkenyl-$R_3$—$(C_2-C_6)$alkenyl-, —$(C_1-C_6)$alkyl-$R_3$—$(C_2-C_6)$alkynyl-, —$(C_2-C_6)$alkenyl-$R_3$—$(C_2-C_6)$alkynyl-, —$(C_2-C_6)$alkynyl-$R_3$—$(C_2-C_6)$alkynyl-, —$(C_2-C_6)$alkynyl-$R_3$—$(C_1-C_6)$alkyl-, or —$(C_2-C_6)$alkynyl-$R_3$—$(C_2-C_6)$alkenyl-, where $R_3$ represents aryl, heteroaryl, $(C_3-C_8)$heterocyclyl, or $(C_3-C_{14})$cycloalkyl, —$(C_1-C_6)$alkyl-OCO—, or —$CH_2$—$(CHOR_3)$$CH_2O$—$(C_1-C_6)$alkyl-, CORM represents a carbonyl metal complex selected from the group consisting of:

$Mn(CO)_5$,

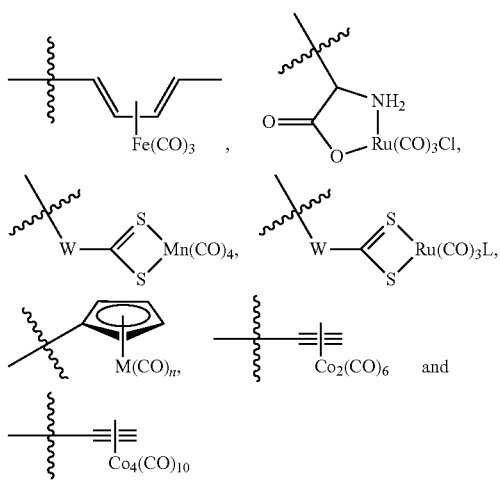

where W represents O or $NR_4$, where $R_4$ represents —$(C_1-C_6)$alkyl-,

L represents an ionic ligand, or a counter-ion,
M represents Rh, Co, Ru, Mn, Mo, V or Fe, and
n is an integer chosen so that the metal M has no free valency,
and $R_1$ represents:
-Q'-Y, where
Q' represents O, S or $NR_5$, where $R_5$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_8)$heterocyclyl, or —$(C_3-C_{14})$cycloalkyl,
Y represents H, —$(C_2-C_6)$alkenyl, -aryl, -heteroaryl, —$(C_2-C_6)$alkynyl, —$(C_3-C_8)$heterocyclyl, —$(C_3-C_{14})$cycloalkyl, —$(C_1-C_6)$alkyl-$R_6$—$(C_1-C_6)$alkyl, —$(C_2-C_6)$alkenyl-$R_6$—$(C_1-C_6)$alkyl, —$(C_1-C_6)$alkyl-$R_6$—$(C_2-C_6)$alkenyl, —$(C_2-C_6)$alkenyl-$R_6$—$(C_2-C_6)$alkenyl, —$(C_1-C_6)$alkyl-$R_6$—$(C_2-C_6)$alkynyl, —$(C_2-C_6)$alkenyl-$R_7$—$(C_2-C_6)$alkynyl, —$(C_2-C_6)$alkynyl-$R_6$—$(C_2-C_6)$alkynyl, —$(C_2-C_6)$alkynyl-$R_6$—$(C_1-C_6)$alkyl, —$(C_2-C_6)$alkynyl-$R_6$—$(C_2-C_6)$alkenyl, $(C_1-C_6)$alkyl-$R_6$, —$(C_2-C_6)$alkenyl-$R_6$, —$(C_2-C_6)$alkynyl-$R_6$, or —$CH_2(CHOR_6)CH_2$—$OR_7$, where $R_6$ represents aryl, heteroaryl, $(C_3-C_8)$heterocyclyl, or $(C_3-C_{14})$cycloalkyl, and where $R_7$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_8)$heterocyclyl, or $(C_1-C_6)$alkyl-$(C_3-C_{14})$cycloalkyl, Or,
A'-CORM' where A' and CORM' are as defined respectively for A and CORM.

11. A pharmaceutical composition comprising at least one pharmaceutically acceptable excipient and at least one compound of formula (I),

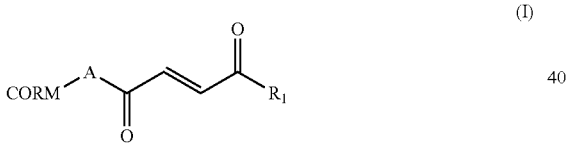

(I)

wherein:
A represents:
a single bond, or
—Z-Q-, where:
Q represents O, S or $NR_2$, where $R_2$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_8)$heterocyclyl, or —$(C_3-C_{14})$cycloalkyl, or $R_2$ and Z are connected to form a $(C_3-C_8)$heterocyclyl,
Z represents —$(C_1-C_6)$alkyl-, —$(C_2-C_6)$alkenyl-, -aryl-, -heteroaryl-, —$(C_2-C_6)$alkynyl-, —$(C_3-C_8)$heterocyclyl-, —$(C_3-C_{14})$cycloalkyl-, —$(C_1-C_6)$alkyl-$R_3$—$(C_1-C_6)$alkyl-, —$(C_2-C_6)$alkenyl-$R_3$—$(C_1-C_6)$alkyl-, —$(C_1-C_6)$alkyl-$R_3$—$(C_2-C_6)$alkenyl-, —$(C_2-C_6)$alkenyl-$R_3$—$(C_2-C_6)$alkenyl-, —$(C_1-C_6)$alkyl-$R_3$—$(C_2-C_6)$alkynyl-, —$(C_2-C_6)$alkenyl-$R_3$—$(C_2-C_6)$alkynyl-, —$(C_2-C_6)$alkynyl-$R_3$—$(C_2-C_6)$alkynyl-, —$(C_2-C_6)$alkynyl-$R_3$—$(C_1-C_6)$alkyl-, or —$(C_2-C_6)$alkynyl-$R_3$—$(C_2-C_6)$alkenyl-, where $R_3$ represents aryl, heteroaryl, $(C_3-C_8)$heterocyclyl, $(C_3-C_{14})$cycloalkyl, —$(C_1-C_6)$alkyl-OCO—, or —$CH_2$—$(CHOR_3)CH_2O$—$(C_1-C_6)$alkyl-, CORM represents a carbonyl metal complex selected from the group consisting of:
$Mn(CO)_5$,

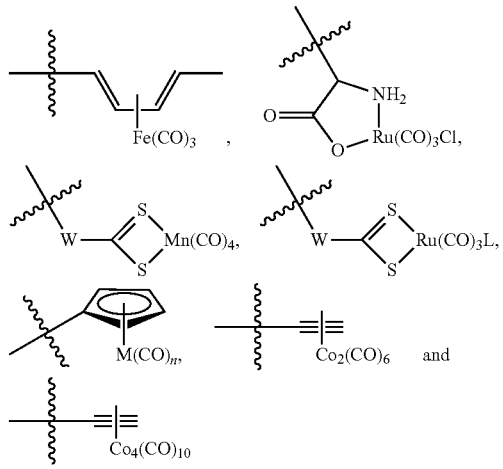

where W represents O or $NR_4$, where $R_4$ represents —$(C_1-C_6)$alkyl-,
L represents an ionic ligand, or a counter-ion,
M represents Rh, Co, Ru, Mn, Mo, V or Fe, and
n is an integer chosen so that the metal M has no free valency,
and $R_1$ represents:
-Q'-Y, where
Q' represents O, S or $NR_5$, where $R_5$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_8)$heterocyclyl, or —$(C_3-C_{14})$cycloalkyl,
Y represents H, —$(C_1-C_6)$alkyl, —$(C_2-C_6)$alkenyl, -aryl, -heteroaryl, —$(C_2-C_6)$alkynyl, —$(C_3-C_8)$heterocyclyl, —$(C_3-C_{14})$cycloalkyl, —$(C_1-C_6)$alkyl-$R_6$—$(C_1-C_6)$alkyl, —$(C_2-C_6)$alkenyl-$R_6$—$(C_1-C_6)$alkyl, —$(C_1-C_6)$alkyl-$R_6$—$(C_2-C_6)$alkenyl, —$(C_2-C_6)$alkenyl-$R_6$—$(C_2-C_6)$alkenyl, —$(C_1-C_6)$alkyl-$R_6$—$(C_2-C_6)$alkynyl, —$(C_2-C_6)$alkenyl-$R_7$—$(C_2-C_6)$alkynyl, —$(C_2-C_6)$alkynyl-$R_6$—$(C_2-C_6)$alkynyl, —$(C_2-C_6)$alkynyl-$R_6$—$(C_1-C_6)$alkyl, —$(C_2-C_6)$alkynyl-$R_6$—$(C_2-C_6)$alkenyl, $(C_1-C_6)$alkyl-$R_6$, —$(C_2-C_6)$alkenyl-$R_6$, —$(C_2-C_6)$alkynyl-$R_6$, or —$CH_2(CHOR_6)CH_2$—$OR_7$, where $R_6$ represents aryl, heteroaryl, $(C_3-C_8)$heterocyclyl, or $(C_3-C_{14})$cycloalkyl, and where $R_7$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_8)$heterocyclyl, or $(C_1-C_6)$alkyl-$(C_3-C_{14})$cycloalkyl, or,
A'-CORM' where A' and CORM' are as defined respectively for A and CORM,
a pharmaceutically acceptable salt, solvate or hydrate thereof.

12. A process for the synthesis of a compound of formula (I) according to claim 1 comprising the reaction of a fumaric acid derivative of formula (IV):

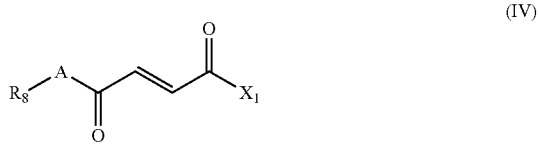

(IV)

wherein:

$X_1$ represents Q'-Y as defined in claim 1, and $R_8$ represents a group selected from the group consisting of:

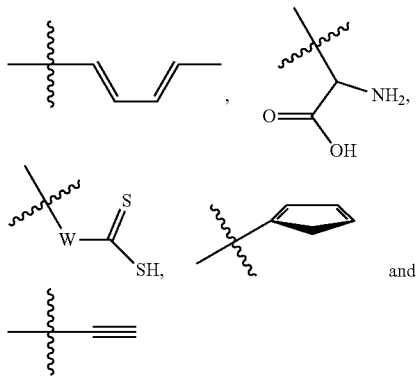

with a carbonyl metal complex of formula $L_1L_2M_x(CO)_y$, where x is 1 or 2 and y is 1 to 10, $L_1$ and $L_2$ represent each a monodentate ligand or $L_1L_2$ represents a bidentate ligand.

13. A process for the synthesis of a compound of formula (I) according to claim 1 comprising the reaction of a fumaric acid derivative of formula (V):

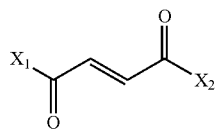
(V)

wherein:

$X_1$ represents Cl, F, Br or an ester, $X_2$ represents Q'-Y, with a compound of formula H-A-CORM, or, the reaction of a compound of formula (V)

wherein $X_1$ represents OH, with a compound of formula Hal-A-CORM where Hal represents a leaving group, A-CORM and Q'-Y being as defined in claim 1.

14. The method of claim 10, wherein the cardiovascular or inflammatory disease is selected from the group consisting of: myocardial ischemia, heart diseases, rheumatoid arthritis, acute and chronic skin wound, inflammatory bowel disease, post-operative ileus, brain ischemia, psoriasis, diabetes, diabetic nephropathy, metabolic syndrome, sickle-cell disease, neurodegenerative diseases, neuropathic pain, hypertension, pulmonary arterial hypertension, septicemia, septic or endotoxic shock, hemorrhagic shock, multiple sclerosis, cancer and chronic obstructive pulmonary disease.

15. The method of claim 10, wherein the cardiovascular or inflammatory disease is selected from the group consisting of: acute and chronic skin wound, brain ischemia, psoriasis, diabetes, metabolic syndrome and multiple sclerosis.

16. The molecule of claim 1, wherein L is a halogen, $BF_4$ or $PF_6$.

17. The molecule of claim 1, wherein M is Co, Ru or Mn.

18. The pharmaceutical composition of claim 11, wherein L is a halogen, $BF_4$ or $PF_6$.

19. The pharmaceutical composition of claim 11, wherein M is Co, Ru or Mn.

* * * * *

UNITED STATES PATENT AND TRADEMARK OFFICE
CERTIFICATE OF CORRECTION

PATENT NO. : 9,944,669 B2
APPLICATION NO. : 15/127674
DATED : April 17, 2018
INVENTOR(S) : Roberto Motterlini et al.

Page 1 of 1

It is certified that error appears in the above-identified patent and that said Letters Patent is hereby corrected as shown below:

In the Specification

Column 9, Line 15:
Replace "$Ru(CO)_3L$" with -- $Mn(CO)_4$ --

In the Claims

Claim 1, Column 43, Line 45:
Replace "-CH" with -- $-CH_2(CHOR_6)CH_2-OR_7$ --

Claim 10, Column 46, Line 37:
Delete "or" before $(C_3-C_{14})$cycloalkyl

Claim 10, Column 47, Line 11:
Insert -- $(C_1-C_6)$alkyl, -- before $(C_2-C_6)$alkenyl Claim 11, Column 48, Line 47:
Replace "$-CH_2(CHOR_6)CH_7-OR_7$" with -- $-CH_2(CHOR_6)CH_2-OR_7$ --

Signed and Sealed this
Fourteenth Day of January, 2020

Andrei Iancu
*Director of the United States Patent and Trademark Office*